United States Patent
Brown

(10) Patent No.: US 8,965,935 B2
(45) Date of Patent: Feb. 24, 2015

(54) SEQUENCE MATCHING ALGORITHM

(75) Inventor: Russell A. Brown, Palo Alto, CA (US)

(73) Assignee: Oracle America, Inc., Redwood Shores, CA (US)

( * ) Notice: Subject to any disclaimer, the term of this patent is extended or adjusted under 35 U.S.C. 154(b) by 1948 days.

(21) Appl. No.: 11/937,315

(22) Filed: Nov. 8, 2007

(65) Prior Publication Data

US 2009/0125514 A1    May 14, 2009

(51) Int. Cl.
*G06F 7/00* (2006.01)
*G06F 19/22* (2011.01)

(52) U.S. Cl.
CPC ..................................... *G06F 19/22* (2013.01)
USPC .......................................... 707/802; 707/807

(58) Field of Classification Search
CPC ............... C12Q 1/6869; C12Q 1/6844; C12Q 2537/165; C12Q 1/6809; C12Q 2535/122; G06F 19/22
See application file for complete search history.

(56) References Cited

U.S. PATENT DOCUMENTS

| | | | |
|---|---|---|---|
| 5,140,321 A * | 8/1992 | Jung | 341/55 |
| 5,701,256 A | 12/1997 | Marr et al. | |
| 2003/0182414 A1* | 9/2003 | O'Neill | 709/223 |
| 2003/0187587 A1* | 10/2003 | Swindells et al. | 702/19 |
| 2008/0222094 A1* | 9/2008 | Cox | 707/3 |

OTHER PUBLICATIONS

"Comparison of Biosequences" by Templw F. Smith and Michael S. Waterman, Advances in Applied mathematics 2, pp. 482-489, 1981.*
"Sequencing XML Data and Query Twigs for Fast Pattern Matching" by Praveen Rao and Bongki Moon, ACM Transactions on Database Systems, vol. 31, No. 1, Mar. 2006, pp. 299-345.*
T. F. Smith, et al., "Identification of Common Molecular Subsequences," Academic Press Inc. (London) Ltd., 1981, pp. 194-197.
James W. Hunt, et al., "A Fast Algorithm for Computing Longest Common Subsequences," Communications of the ACM, vol. 20, 1977, pp. 350-353.
Nicklaus Wirth, "Algorithms + Data Structures = Programs," Prentice-Hall 1976, pp. 215-226.
Dan Gusfield, "Algorithms on Strings, Trees and Sequences," Chapter 11, Cambridge University Press, 1997, pp. 215-253.

* cited by examiner

*Primary Examiner* — Fred I Ehichioya
*Assistant Examiner* — Hasanul Mobin
(74) *Attorney, Agent, or Firm* — Meyertons, Hood, Kivlin, Kowert & Goetzel, P.C.; Paul T. Seegers; Dean M. Munyon

(57) ABSTRACT

Sequence alignment techniques are disclosed. In one embodiment, a sparse data structure is constructed that represents respective character positions of matching character sets in input sequences. This sparse data structure may take a variety of forms, including a "tree of trees." Once constructed, each match is linked to at most one other match using a local application of a predetermined algorithm (e.g., a Smith-Waterman-type scoring algorithm). The links between matches are analyzed and a possible alignment or set of alignments is produced.

18 Claims, 22 Drawing Sheets

|   | v | i | n | t | n | e | r |
|---|---|---|---|---|---|---|---|
| g | 0 | 0 | 0 | 0 | 0 | 0 | 0 |
| r | 0 | 0 | 0 | 0 | 0 | 0 | X |
| i | 0 | X | 0 | 0 | 0 | 0 | 0 |
| n | 0 | 0 | X | 0 | X | 0 | 0 |
| d | 0 | 0 | 0 | 0 | 0 | 0 | 0 |
| e | 0 | 0 | 0 | 0 | 0 | X | 0 |
| r | 0 | 0 | 0 | 0 | 0 | 0 | X |

102A (columns), 102B (rows), 122

*FIG. 1C*

146 — $S_{(x,y)} = \max\{\text{Diagonal Score, Row Score, Column Score, 0}\}$

146A — Diagonal Score = $S_{(x-1,y-1)} + \text{Mapping}_{(x,y)}$

146B — Row Score = $\max\limits_{x>j>0} \{S_{(x-j,y)} - \text{Row Gap Score}_{(x,y)(x-j,y)}\}$ 146C — Column Score = $\max\limits_{y>k>0} \{S_{(x,y-k)} - \text{Column Gap Score}_{(x,y)(x,y-k)}\}$ 146D — Row Gap Score$_{(x,y)(x-j,y)}$ = 8+j 146E — Column Gap Score$_{(x,y)(x,y-k)}$ = 8+k

*FIG. 1E*

Mapping /— 142

|   | v  | i  | n  | t  | n | e | r |
|---|----|----|----|----|---|---|---|
| g | -3 | -3 | -3 | -3 |   |   |   |
| r | -3 | -3 | -3 | -3 |   |   |   |
| i | -3 | 5  | -3 | -3 |   |   |   |
| n | -3 | -3 | 5  | -3 |   |   |   |
| d |    |    | ↑  |    |   |   |   |
| e |    | Mapping$_{(4,4)}$ |  |  |   |   |   |
| r |    |    |    |    |   |   |   |

Scoring Matrix /— 150

|   |   | v | i | n | t | n | e | r |
|---|---|---|---|---|---|---|---|---|
|   | 0 | 0 | 0 | 0 | 0 |   |   |   |
| g | 0 | 0 | 0 | 0 | 0 |   |   |   |
| r | 0 | 0 | 0 | 0 | 0 |   |   |   |
| i | 0 | 0 | 5 | 0 | 0 |   |   |   |
| n | 0 | 0 | 0 | 10| 1 |   |   |   |
| d |   |   |   | ↑ |   |   |   |   |
| e |   |   |   | $S_{(4,4)}$ |   |   |   |   |
| r |   |   |   |   |   |   |   |   |

147A — Diagonal Score = $S_{(3,3)}$ + Mapping$_{(4,4)}$ = 0-3 = -3

147B — Row Score = max {$S_{(3,4)}$ − Gap Score$_{(3,4)}$, $S_{(2,4)}$ − Gap Score$_{(2,4)}$, $S_{(1,4)}$ − Gap Score$_{(1,4)}$}
= max {10-8-1, 0-8-2, 0-8-3} = 1

147C — Column Score = max {$S_{(4,3)}$ − Gap Score$_{(4,3)}$, $S_{(4,2)}$ − Gap Score$_{(4,2)}$, $S_{(4,1)}$ − Gap Score$_{(4,1)}$}
= max {0-8-1, 0-8-2, 0-8-3} = -9

149 — $S_{(4,4)}$ = max {-3, 1, -9, 0} = 1

*FIG. 1F*

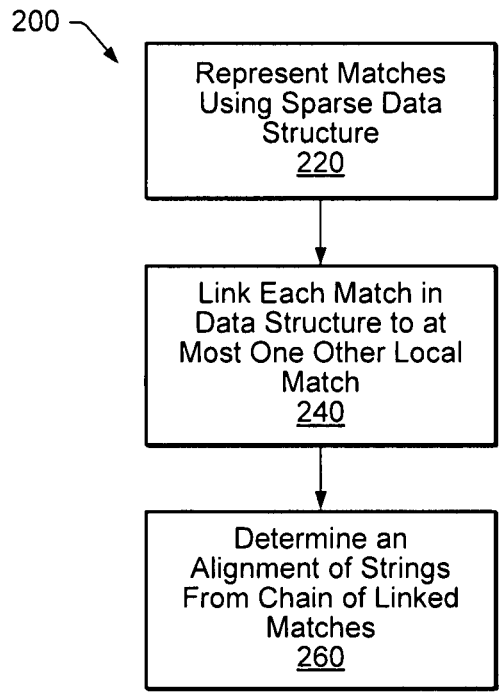
FIG. 2
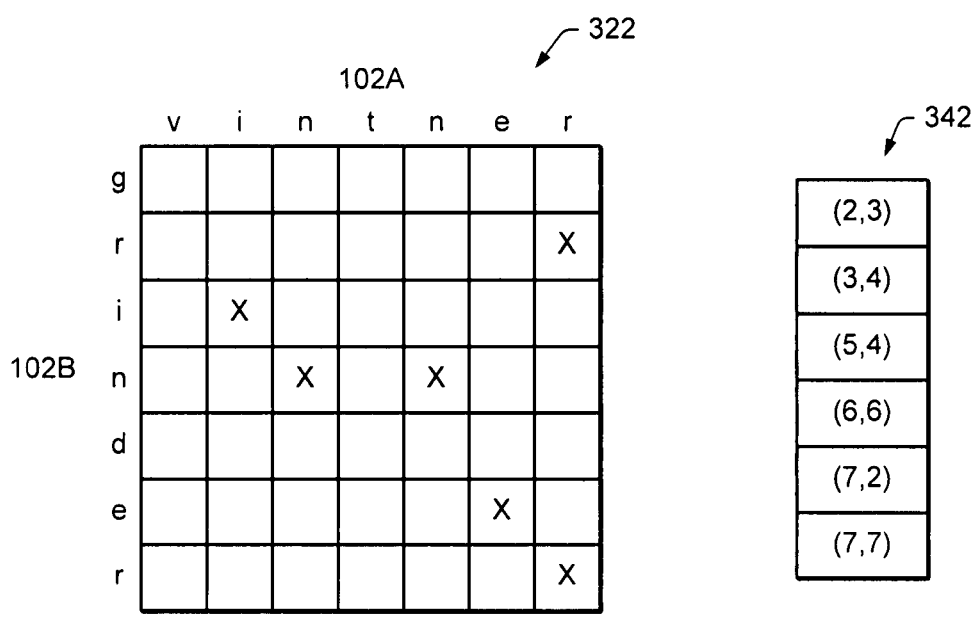
FIG. 3A
FIG. 3B

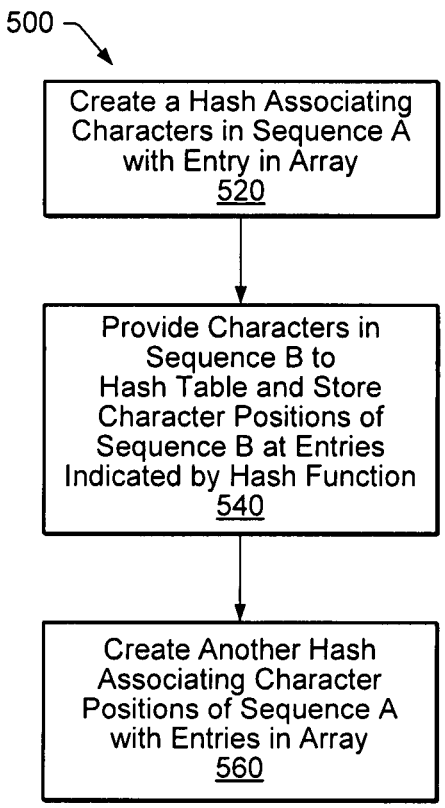
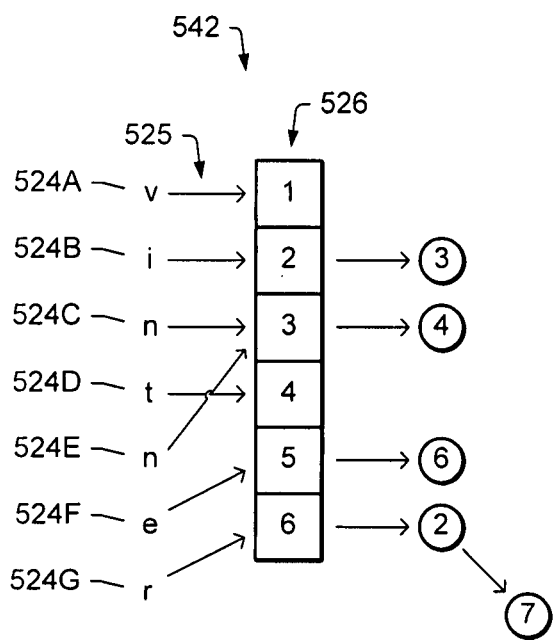
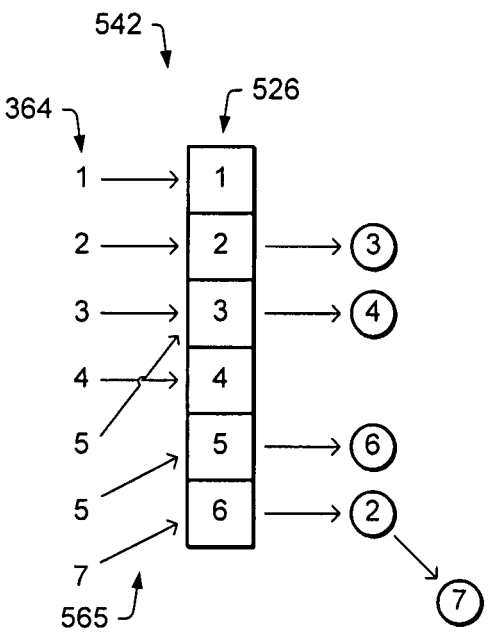
FIG. 5A
FIG. 5B
FIG. 5C mismatch = -3   space = -8-c   match = +5 v - i n t n e r
g r i n d - e r

104A

SEQUENCE MATCHING ALGORITHM

BACKGROUND

1. Field of the Disclosure

This disclosure relates to alignment or matching of sequences, e.g., strings of characters.

2. Description of the Related Art

It is frequently desired to "align" two sequences for the purpose of determining similar portions of these sequences. Alignment includes introducing "gaps" into one or both sequences in a manner that optimizes the similarity between the two sequences. This functionality is used, for example, to determine similar regions of two nucleotide or protein sequences.

One algorithm that has been used for sequence matching is the Smith-Waterman algorithm. See T. F. Smith and M. S. Waterman, *Identification of Common Molecular Subsequences*, J. Mol. Biol. (1981) 147, 195-97. Sequence matching is commonly performed on very long sequences, e.g., sequences over $2^{23}$ characters in length. Performing matching of such sequences using the Smith-Waterman algorithm is very computationally intensive—on the order of MN (denoted as "O(MN)"), where M and N are the lengths of the two sequences being matched. As a result, the use of the Smith-Waterman algorithm is not practical in many instances. A less computationally intensive method for sequence matching is therefore desired.

SUMMARY

Various embodiments for performing an alignment of input sequences are disclosed. In one embodiment, matches between a first and second sequence are represented in a sparse data structure, the matches are linked to at most one other match, and one or more sequences of linked matches are selected, wherein the selected sequences of linked matches are usable do determine an alignment of in the input sequences. In some embodiments, the data structure may be a tree of trees or a hash table. The tree of trees may be self-balancing. In one embodiment, the algorithm uses a Smith-Waterman-type scoring scheme. In some embodiments, matches may be between multiple characters. Furthermore, matching may be performed according to various algorithms, including those that use synonyms. In one embodiment, matches may be represented in the sparse data structure as an (x,y) coordinate pair where x is the character position of the match in the first sequence and y is the character position in the second sequence. In one embodiment, the sequences of linked matches are those sequences having the highest cumulative link score.

In one embodiment, a given match within a data structure may be linked to at most one other match in the data structure by traversing a selected region of an (x,y) coordinate space that is local to the (x,y) coordinate pair representing the given match. The region may, in one embodiment, be a square. In one embodiment, sub-regions of the selected region are selected until a sub-region is found that includes at least one match. In one embodiment, if multiple matches are found within a current sub-region, a single match is selected according to some algorithm (e.g., selecting the match having the highest score according to a Smith-Waterman-type scoring scheme).

Various embodiments include systems, methods, and computer-readable media for performing techniques disclosed herein.

BRIEF DESCRIPTION OF THE DRAWINGS

FIG. 1C depicts an example of a dense data structure.

FIG. 1E depicts formulae used in a Smith-Waterman scoring algorithm.

FIG. 1F depicts an example calculation for an entry in a scoring matrix.

FIG. 2 is a flowchart of one embodiment of a method for aligning two input sequences.

FIG. 3A depicts a matrix used to illustrate differences between a sparse data structure and a dense data structure.

FIG. 3B depicts one embodiment of a sparse data structure implemented using a list.

FIG. 5A is a flowchart of one embodiment of a method for building a sparse hash table.

FIGS. 5B-C depict an example of a sparse hash table.

DETAILED DESCRIPTION

This specification includes references to "one embodiment" or "an embodiment." The appearances of the phrases "in one embodiment" or "in an embodiment" do not necessarily refer to the same embodiment. Particular features, structures, or characteristics may be combined in any suitable manner in one or more embodiments.

In order to appreciate the sequence-matching algorithm of the present disclosure, it is instructive to consider, in FIGS. 1A-1J, an example of sequence matching using techniques described in Smith and Waterman's 1981 paper referenced above.

Figure 1A:
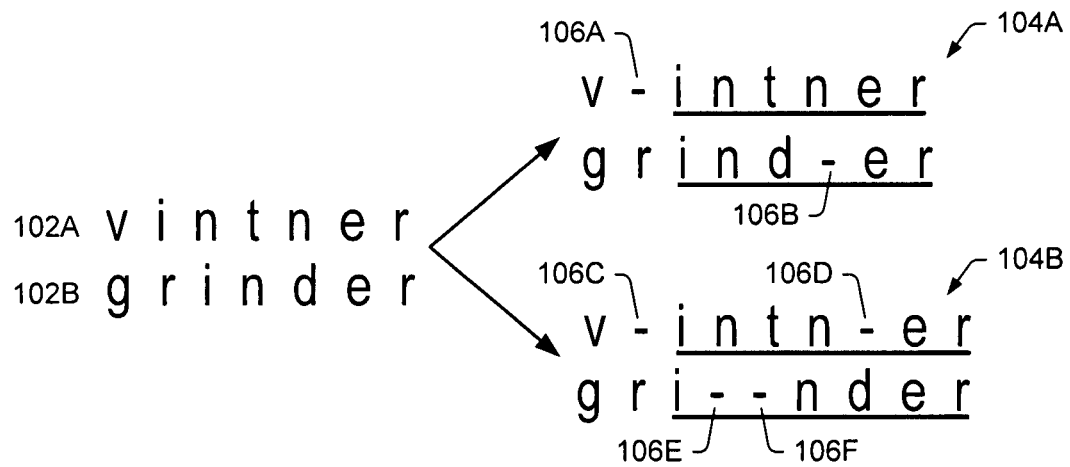
FIG. 1A depicts an example of two input sequences and two possible alignments of those sequences.

Turning now to FIG. 1A, two example sequences 102A and 102B to be aligned are shown. Sequence 102A is the alphabetic string "vintner," while sequence 102B is the string "grinder." Sequences 102A and 102B are used an example sequences throughout the present disclosure. These sequences can, of course, be any arbitrary sequence, composed of any particular "alphabet." For example, a sequence can be a binary sequence (where each position is either 0 or 1), a sequence of nucleotides (where each position can be Adenine (A), Thymine (T), Cytosine (C) or Guanine (G)), an alphabetic sequence (where each position is A-Z or a-z), etc. The goal of sequence matching is to determine an alignment of the two strings by inserting "gaps" into one or both sequences 102 in order to produce an "optimal" match according to some predetermined criteria (e.g., a Smith-Waterman-type scoring algorithm, discussed below). FIG. 1A shows two possible alignments 104 of sequences 102. In alignment 104A, gaps 106A and 106B are introduced between the "v" and "i" of sequence 102A and between the "d" and "e" of sequence 102B, respectively. By way of contrast, alignment 104B includes gaps 106C-F that are positioned differently relative to alignment 104A. As will be discussed below, alignment 104A has a higher Smith-Waterman score than alignment 104B, and therefore may be preferred to alignment 104B in some instances.

Figure 1B:
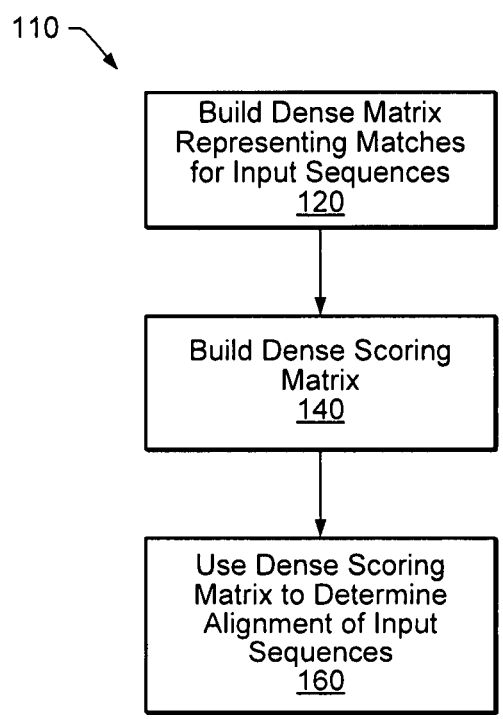
FIG. 1B is a flowchart of one embodiment of a method for a Smith-Waterman sequence-matching algorithm.

Turning now to FIG. 1B, a flowchart of a method 110 is shown. Method 110 is one embodiment of a Smith-Waterman sequence-matching algorithm. Given two input sequences (e.g., sequences 102), a data structure (e.g., a matrix) is built in step 120 that indicates matches and mismatches between the various character positions of the two input sequences. The data structure in step 120 is "dense" in that it includes m×n entries, where m and n are the number of characters in the two input sequences. Next, in step 140, another dense matrix is constructed that includes a "Smith-Waterman score" for each location in the structure. Finally, in step 160, the dense scoring matrix is used to produce an alignment of the input. The sequence matching algorithms described below (including with reference to FIGS. 2-10) include improvements relative to method 110, including more efficient sequence matching techniques.

Turning now to FIG. 1C, an example dense data structure is shown—a matrix 122. In the example shown here, columns in matrix 122 correspond to character positions in sequence 102A ("vintner"), while rows in matrix 122 correspond to character positions in sequence 102B ("grinder"). Each entry in matrix 122 indicates whether a match ("x") or mismatch ("o") exists between respective character positions in sequences 102.

As will be described below, sequence matching algorithms of the present disclosure recognize that a particular entry in matrix 122 can be represented by a coordinate pair, in which the first coordinate refers to a character position in the first input sequence and the second coordinate refers to a character position in the second input sequence. A coordinate pair is also referred to herein as an "x,y coordinate" or a coordinate in an (x,y) coordinate space, where x represents the character position within a first input sequence and y represents the character position within a second input sequence. For example, the entry at column 2, row 3 in matrix 122 indicates that there is a match between the "i" in "vintner" and the "i" in "grinder." Similarly, the entry at column 6, row 7 in matrix 122 indicates that there is a mismatch between the "e" in "vintner" and the "r" in "grinder."

Figure 1D:
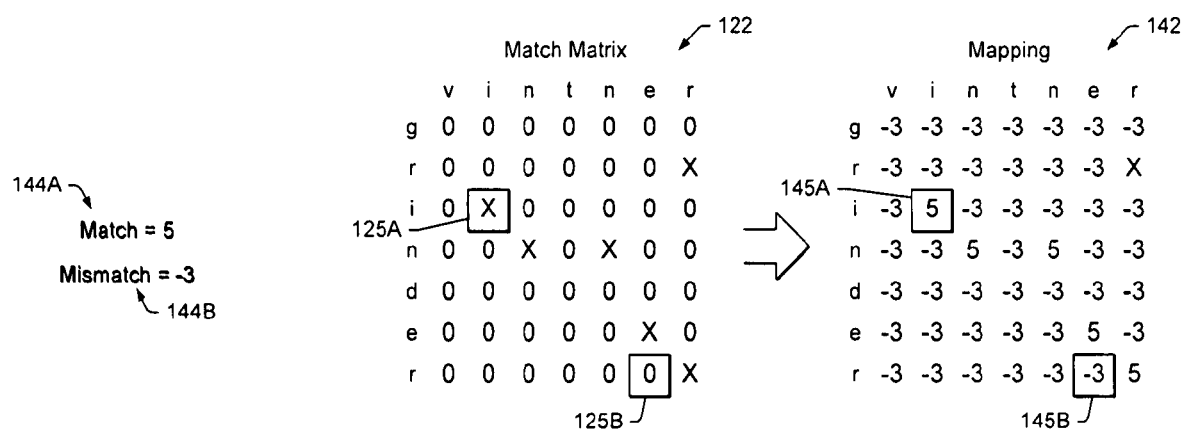
FIG. 1D depicts an example of possible scoring criteria for sequence matching.

Turning now to FIG. 1D, an example of a mapping matrix 142 used in the Smith-Waterman algorithm is shown. Mapping matrix 142 is generated from matrix 122 according to criteria 144, in which a match is represented by +5, and a mismatch by −3. Mapping matrix 142 can be generated from matrix 122 and criteria 144. For example, in matrix 122, entry 125A at column 2, row 3 contains a match, so corresponding mapping entry 145A in matrix 142 contains a score of 5. Entry 125B at column 6, row 7, however, indicates a mismatch; its corresponding entry 145B in matrix 142 therefore contains a score of −3.

Given mapping matrix 142, a corresponding scoring matrix S is then computed. (Scoring Matrix S or 150 is described further below with reference to FIG. 1F.) Each entry in the scoring matrix may be computed using predetermined formulae. For example:

$$S_{(x,y)} = \max\{\text{Diagonal Score, Row Score, Column Score, 0}\} \quad (146)$$

$$\text{Diagonal Score} = S_{(x-1,y-1)} + Mapping_{(x,y)} \quad (146A)$$

$$\text{Row Score} = \max_{x>j>0} \{S_{x-j,y} - \text{Row Gap } Score_{(x,y)(x-j,y)}\} \quad (146B)$$

$$\text{Column Score} = \max_{y>k>0} \{S_{(x,y-k)} - \text{Column Gap } Score_{(x,y)(x,y-k)}\} \quad (146C)$$

$$\text{Row Gap } Score_{(x,y)(x-j,y)} = 8 + j \quad (146D)$$

$$\text{Column Gap } Score_{(x,y)(x,y-k)} = 8 + k \quad (146E)$$

(These formulae are also shown for convenience in FIG. 1E.) $S_{(x,y)}$ is the score for an entry (x, y) in the scoring matrix. (As described above, "x" and "y" correspond to a column and row, respectively, in the scoring matrix.) As indicated in formula 146, $S_{(x,y)}$ is equal to the maximum of four quantities: a diagonal score 146A, a row score 146B, a column score 146C, and zero (thus guaranteeing in one embodiment that there are no negative scores in the scoring matrix). $S_{(4,4)}$ therefore represents the entry in the scoring matrix found at column 4, row 4.

As shown above, diagonal score 146A for a scoring matrix entry $S_{(x,y)}$ is the sum of the adjacent, diagonal entry $S_{(x-1,y-1)}$ and the corresponding entry in mapping matrix 142, $Mapping_{(x,y)}$. Row score 146B is the maximum of a set of difference values. Each difference value is given by the formula $S_{(x-j,y)}$—Row Gap $Score_{(x,y)(x-j,y)}$, where x>j>0 within the set. Row Gap Score is computed using formula 146D, and is simply the distance between two points on a given row plus a constant (e.g., 8). Thus, for each difference value in the set, a row gap score is computed between the point for which a score is being calculated (e.g., entry (4,4)) and the point on that row corresponding to the current value of j. Similarly, column score 146C is also the maximum of a set of difference values. Each difference value is given by the formula $S_{(x,y-k)}$—Column Gap $Score_{(x,y)(x,y-k)}$, where y>k>0 within the set. Column Gap Score is computed using formula 146E in a manner similar to the computation of the Row Gap Score.

Turning now to FIG. 1F, an example calculation for $S_{(4,4)}$ (entry 4,4) in a scoring matrix S (150) is shown. Because of the nature of the scoring algorithm, formulae for computation of an entry such as $S_{(1,1)}$ uses previous values, e.g., $S_{(0,0)}$.

Accordingly, the $0^{th}$ row and column of the matrix (shown outside the dotted line if FIG. 1F) are filled with zeroes. This "dummy" row and column are not shown in FIGS. 1G, 1H, and 1J for convenience. This example presumes that all entries $S_{(x,y)}$ that are "prior" to $S_{(4,4)}$ in matrix 150 have previously been computed (that is, all values $S_{(x,y)}$ have been computed, where x<4 and y<4, as shown in FIG. 1F).

Using formulae 146, a diagonal score 147A, a row score 147B, and a column score 147C are determined. As shown at 149, these three scores are −3, 1, and −9. The entry $S_{(4,4)}$ is thus computed to be the maximum of these three scores and zero, resulting in a score of 1.

Diagonal score 147A for $S_{(4,4)}$ is computed from the sum of the corresponding entry (4,4) in mapping matrix 142 (Mapping$_{(4,4)}$) plus the adjacent entry along the diagonal of 150: $S_{(3,3)}$. Row score 147B is computed as follows: As indicated in formula 146B, the row score is the maximum of a set of difference values. Each of these values is the difference between 1) a previously computed value in the scoring matrix ($S_{x-j,y}$) and 2) a row gap score between that entry ($S_{x-j,y}$) and the entry for which the score is ultimately being computed ($S_{x,y}$) The number of entries in the set is determined by the number of positions in row y between the $0^{th}$ column and the column of the entry for which the score is ultimately being computed ($S_{x,y}$). For example, where the entry for which the score is ultimately being computed is in the fourth column, the row score is the maximum of three values, since there are three columns between the $0^{th}$ column and the $4^{th}$ column (see circled row in scoring matrix 150). In this example, the value j can be considered to correspond to the current column, where j is successively set to 1, 2, or 3 for each of the entries in the set of difference values in computing row score 147B. The first difference value (j=1) is computed for row score 147B using the formulae 146B and 146D: $S_{(x-j,y)}$—Row Gap Score$_{(x,y)(x-j,y)}$. The value $S_{(x,y-j)}$ is the previously computed entry at $S_{(4,3)}$, or 10. The row gap score is 8 plus the distance between (4,3) and (4,4), or 9. Accordingly, the first difference value in the set of values from which row score 147B is calculated is 1. Two additional difference values are calculated as shown in FIG. 1F (−10, −11). The maximum of this set is 1. Column score 147C is computed in a similar manner. A scoring methodology such as that shown in FIG. 1E is referred to herein as a "Smith-Waterman-type scoring scheme."

Figures 1G, 1H, 1J:
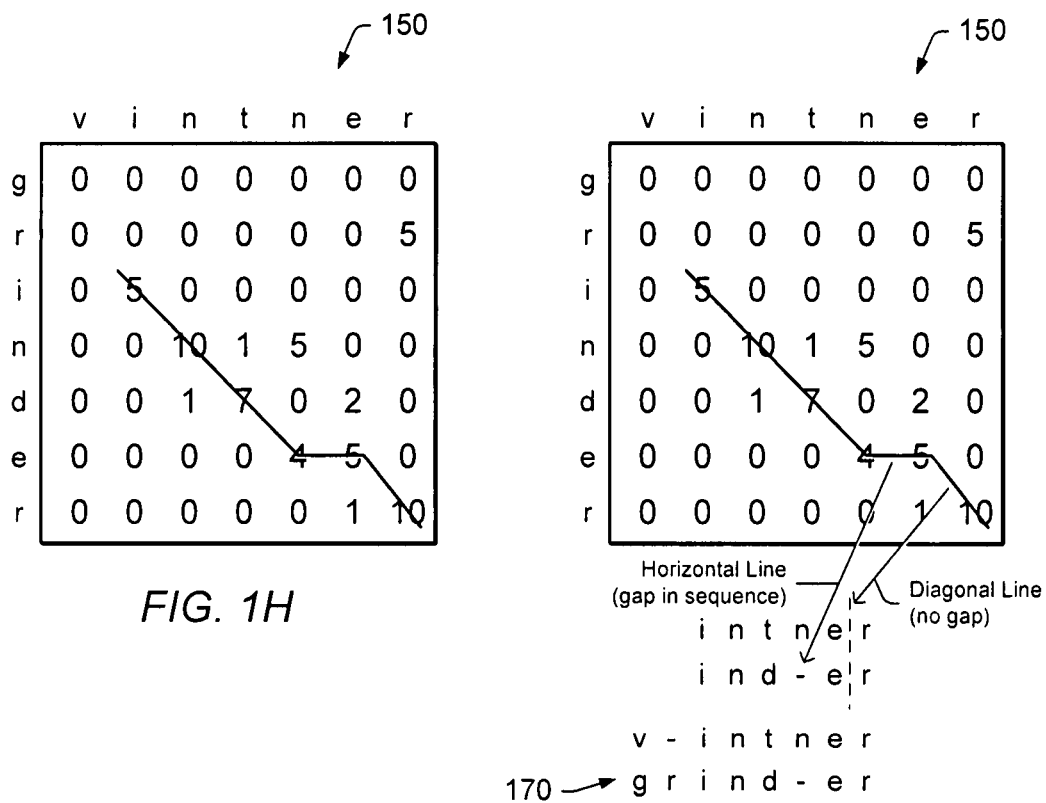
FIG. 1G depicts an example of a completed scoring matrix.
FIG. 1H depicts an example of linking entries in the completed scoring matrix of FIG. 1G.
FIG. 1J illustrates how linked matches may determine the placement of gaps in an alignment of two input sequences.

Turning now to FIG. 1G, a view of the completed scoring matrix 150 from FIG. 1F is shown.

Turning now to FIG. 1H, an example 170 of linking various entries in scoring matrix 150 is shown. Starting from the lower right in scoring matrix 150, the highest score is located (here, the score 10 in column 7, row 7). From this starting point, the adjacent entries that are up and to the left of the starting point are examined to determine whether any entries have non-zero scores. If so, the entry with the highest score is selected, in effect linking that entry to the entry at the starting point. (Here, this is represented by a line from column 7, row 7 (10) to column 6, row 6 (5). This process is then repeated using the linked entry (6,6), resulting in a link to entry (5,6). The process repeats until no adjacent entries that are "up and to the left" of the current entry have non-zero scores. In FIG. 1H, entry (2,3) is not linked to any adjacent entries.

Turning now to FIG. 1J, the direction in which entries in matrix 150 are linked determines whether and where gaps are inserted in sequences 102. If two adjacent entries are linked by a diagonal line, this indicates that no gaps are to be inserted between the characters corresponding to these entries in either sequence 102A or 102B. This can either represent a match or a mismatch. For example, since there is a diagonal line directly between two successive matches: entries 7,7 and 6,6. No gaps 106 are inserted between "e" and "r" in either sequence 102. Conversely, the diagonal line from score 4 (entry (5,6)) to score 7 (entry (4,5)) is indicative of two mismatched characters: the "t" in "vintner" and the "d" in "grinder."

On the other hand, if two adjacent entries are linked by a horizontal line (e.g., scores 4 and 5 in (6,6) and (5,6) respectively), this indicates that a gap is to be inserted in sequence 102B but not 102A. The linking of two adjacent entries by a vertical line (not shown in FIG. 1J) indicates that a gap is to be inserted in sequence 102A but not sequence 102B.

The sequence of linked entries in FIG. 1J spans the common "i" to the common "r" in the two input sequences 102. The leading characters in both sequences may then be appended to the linked entries using a variety of techniques, as indicated by reference numeral 170.

Turning now to FIG. 2, a flowchart of a method 200 is shown. Method 200 is one embodiment of a proposed sequence-matching algorithm that offers efficiency vis-à-vis Smith-Waterman techniques described above. In one embodiment, method 200 takes as input two sequences (e.g., sequences 102).

First, in step 220, matches between the various character positions of the two input sequences are represented using a "sparse" data structure. Step 220 is described in greater detail with reference to FIGS. 3A-E below. Next, in step 240, each match in the sparse data structure is linked to at most to one other match, using a local application of some predetermined algorithm (e.g., an algorithm based in whole or part on a Smith-Waterman-type scoring scheme). Step 240 is described in greater detail with reference to FIGS. 4-7 below. Finally, in step 260, an alignment is produced using a "chain" of links determined in step 240. Step 260 is described in greater detail with reference to FIGS. 8A-C below.

As used herein, a "match" refers to one or more characters ("a character set") at some position in a first input sequence meeting some predetermined criteria relative to one or more other characters at some position in a second input sequence. Thus, a match may be based on a comparison of one character in each input sequence, or more than one character. In many embodiments, this predetermined criterion is whether the two character sets are identical (e.g., "a" in first input sequence equals "a" in second input sequence or "ab" in first input sequence equals "ab" in second input sequence)—the term "match" is not limited to this criterion, however. A match can be case insensitive, for example (that is, "a" can match "a" or "A"). A match can also be based on the use of "synonyms"—two dissimilar character sets can be said to match based on some predefined criteria. For example, in the field of genetic research, different codons that map the same amino acid may constitute a match in some embodiments. These different codons can thus be considered "synonyms" of one another.

Method 200 does not necessarily produce the "optimal" alignment between sequences 102, but can produce a sequence alignment much faster than the Smith-Waterman algorithm. This increase in speed is due in part to the use of a "sparse" data structure (as opposed to a "dense" data structure) and to the fact that, in method 200, each match is linked using a local algorithm to at most one other match (as opposed to a global algorithm in which a match may be linked to an arbitrary number of other matches). The greatly reduced computational complexity of method 200 is discussed further below.

As described above, step 220 in method 200 includes building a sparse data structure. As used herein, a "sparse" data structure is one that does not require, for matching of a first sequence of M characters with a second sequence of N characters, a data structure (e.g., a matrix, array, etc.) of M×N entries. In some embodiments, a sparse data structure is one having entries indicative of only of matches (and not mismatches) between characters in two sequences being aligned. For example, consider FIG. 3A. FIG. 3A shows a 7×7 matrix 322 indicating matches between the sequences "vintner" and "grinder." In matrix 322, 6 entries are designated as matches. As described below, in some embodiments, a sparse data structure would include only entries for the six matches shown in FIG. 3A. A dense data structure, on the other hand, would include 49 entries, indicating either a match or a mismatch for each possible combination of character positions.

In some embodiments, a sparse data structure may simply contain a number of entries E that is considerably less than the M×N, where M and N are the number of characters in the respective sequences being aligned. Thus, a particular data structure would still be sparse if it contained, for example, a small number entries indicative of mismatches, as long as the total number of entries E<<M×N. For example, if a data structure representing the matches shown in FIG. 3A included 6 entries indicating matches and a small number of entries (e.g., 2) indicative of mismatches, the data structure would still be considered "sparse," as that term is used herein.

A sparse data structure may, of course, include other information (e.g., header information) not related to matches or mismatches. By the same token, a sparse data structure may be part of a larger data structure with unrelated or other information and still be considered "sparse" within the meaning of this disclosure.

In many instances, a sparse data structure has a significantly smaller memory footprint than a dense data structure. Consider, however, that if sequence A of M characters is identical to sequence B of N characters (M=N), the resultant data structure representing matches between the two sequences will be of size M×N. Such a data structure can still be considered sparse, however, if it is not required to have M×N entries (in contrast, for example, to the data structure in FIG. 1C, which has M×N entries for all possible input sequences).

As will be described below, a sparse data structure includes information indicative of matches between two sequences. In one set of embodiments, the information representing each match may be a pair of coordinates indicating the respective character positions of the sequences that match. For example, the match between the second "n" in "vintner" and the "n" in "grinder" may be represented as (5,4), as the second "n" in "vintner" is in the fifth character position and "n" is the fourth character in "grinder." As described above, a coordinate pair may also be referred to as an "x,y coordinate," where x represents the character position in the first sequence (which can also be considered conceptually to correspond to the xth column of a matrix for the two sequences), and where y represents the matching character position in the second sequence (which can also be considered to correspond to the yth row of the same conceptual matrix). As will be described below, the use of coordinate pairs to represent matches allows for "distance" computations between matches.

Various possible sparse data structures are now described with reference to FIGS. 3B-3E.

Turning now to FIG. 3B, the use of a list 342 as a sparse data structure is illustrated. List 342 contains coordinate pairs that correspond to each of a set of matches. For example, the first entry (2,3) represents the match between the second character position in "vintner" ("i") and the third character position in "grinder" ("i"). List 342 can, of course, be implemented in a variety of ways (array, linked list, queue, stack, etc.). To add a match, a coordinate pair may simply be appended to the list. (Other variations are possible as well.) Similarly, entries may be deleted from the list. To search for a match, the coordinates of the desired match are compared (e.g., sequentially) to each entry 342, e.g., starting at the beginning and progressing through the list.

Figure 3C:
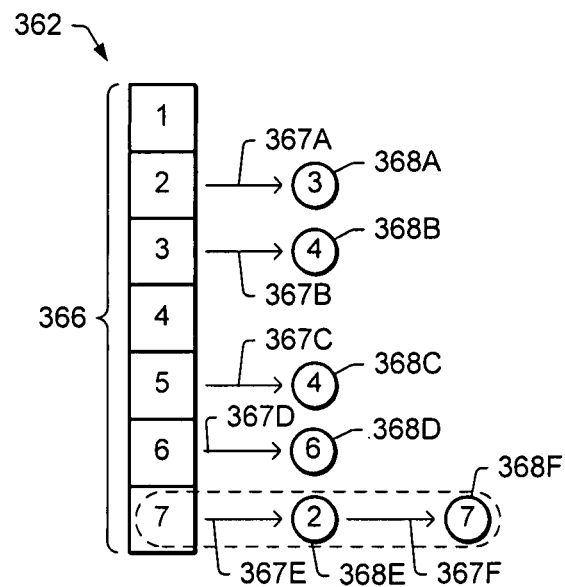
FIG. 3C depicts one embodiment of a sparse data structure implemented using a map.
Figure 3D:
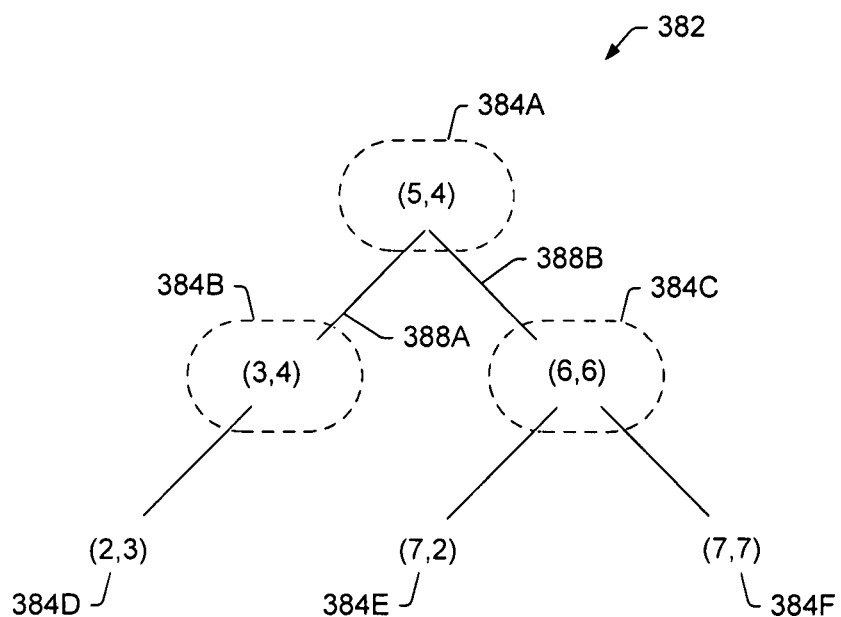
FIG. 3D depicts one embodiment of a sparse data structure implemented using a tree.

Turning now to FIG. 3C, the use of a map 362 as a sparse data structure is illustrated. Map 362 can be implemented in a variety of ways (as a table, hash table, graph, etc.). In the embodiment shown in FIG. 3C, map 362 contains all possible x values as entries 366 (even those x positions for which there are no matches in the second input sequence). (Alternate embodiments are possible in which there are not entries for x coordinates for which there are no matching y coordinates). For those characters in sequence A for which there is a match in sequence B, entries 366 may include a pointer 367 to a corresponding y coordinate 368 (indicating a character position in sequence B). Note that a given entry 366 may point to more than one y coordinate (e.g., entry "7" points to y coordinate 368E, which in turn points to y coordinate 368F). As with list 342, entries may be added and deleted to map 362. Searching map 362 may be performed by using the desired x coordinate as an index, and then progressing through the y coordinate chain (if any).

A sparse data structure may also be implemented as a tree-based data structure. Consider FIG. 3D, which illustrates one example of such a structure. Generally speaking, a tree is a data structure built from nodes (indicated by reference numerals 384 in FIG. 3D). Each node includes a data entry (here, a coordinate pair) and one or more pointers 388 to other nodes 384. Tree 382 is implemented as a binary tree, and thus has two "branches." The left branch is pointed to by pointer 388A, while the right branch is pointed to by pointer 388B. Thus, "left" pointer 388A connects "parent" node 384A to "child" node 384B, and "right" pointer 388B connects "parent" node 384A to "child" node 384C. A node that is not another node's "child" is commonly referred to as the "root" (here, node 384A is the root node). Similarly, nodes that have no "children" (e.g., nodes 384D-F) are commonly referred to as "leaves."

A sparse data structure may implemented using any of various types of tree structures. For example, a sparse data structure may be implemented as a space-partitioning tree (e.g., a kd-tree), a self-balancing binary search tree (e.g., AVL tree, red-black tree), etc.

In a binary search tree, data entries can be compared using some predefined criteria. For example, if a child node's data entry is less than (which may be defined in many different ways) its parent node's data entry, the child node may be joined to the parent node using the parent node's left pointer (alternately, the right pointer could be used). Conversely, a child node having a data entry greater than its parent node's data entry can be linked by the parent's right (or left) pointer. The tree 382 depicted in FIG. 3D has entries with x coordinates less than 5 on the left branch, and entries with x coordinates greater than 5 on the right branch.

The structure of a binary search tree allows entries to be added to the structure easily. For example, an entry to be added to the tree is compared against an existing node (e.g., 384A). If the value of the new entry is less than the value of the current node being compared against, the entry will be added somewhere on the left branch of the tree; otherwise it will be added somewhere on the right branch. Suppose it is determined that the new entry's value is less than that of root node 384A. If the left pointer of node 384A is not currently pointing to another node, the left pointer will be set to point to the new node. If, however, the left pointer of 384A is pointing to another node 384, the value of this node is then used as a point of comparison for the value of the new entry. This process is repeated until an unused left or right pointer is found at which to insert the new entry.

Searching for a particular entry in a binary tree is similar to the process for adding an entry. Comparisons are performed (in the same manner described above) until either a match or unused pointer is encountered. If a match is found, the entry exists in the tree. Otherwise, the entry does not exist in the tree.

A "balanced" tree is one in which no branch (where a "branch" is a sequence of linked nodes starting from the root node and ending with a leaf node) differs in length from another branch by more than one. For example, data structure 382 is balanced because every branch has a length of 3 (e.g., 5,4→3,4→2,3). For a generic tree structure, as entries are added, one or more branches may become significantly longer than others, which may result in sub-optimal search times. Accordingly, certain tree structures are "self-balancing," meaning that nodes are inserted/deleted according to algorithms that maintain the balance of the tree. Examples of self-balancing tree structures are AVL trees and red-black trees.

As described above, in one embodiment sequence matching method 200 includes the use of a data structure that stores coordinate (x,y) pairs to represent matches. One type of tree designed to store k-dimensional coordinates is referred to as a kd-tree. A kd-tree is a balanced binary tree specifically designed for processing coordinate pairs. A kd-tree is not self-balancing, however. Instead, to construct a kd-tree from a set of coordinate pairs, a "central-most" coordinate pair is selected and is chosen as the root node. Additional matches are then appended to the tree using predefined comparison criteria determined using a node's location and its proximity to other nodes. Additions to and searches of a kd-tree are performed in the same manner as described above for a binary search tree. Accordingly, when it is desired to add nodes to a kd-tree, the tree is not guaranteed to remain balanced. Alternately, a new kd-tree can be constructed each time the tree becomes unbalanced. Either of these results is less than ideal.

Figure 3E:
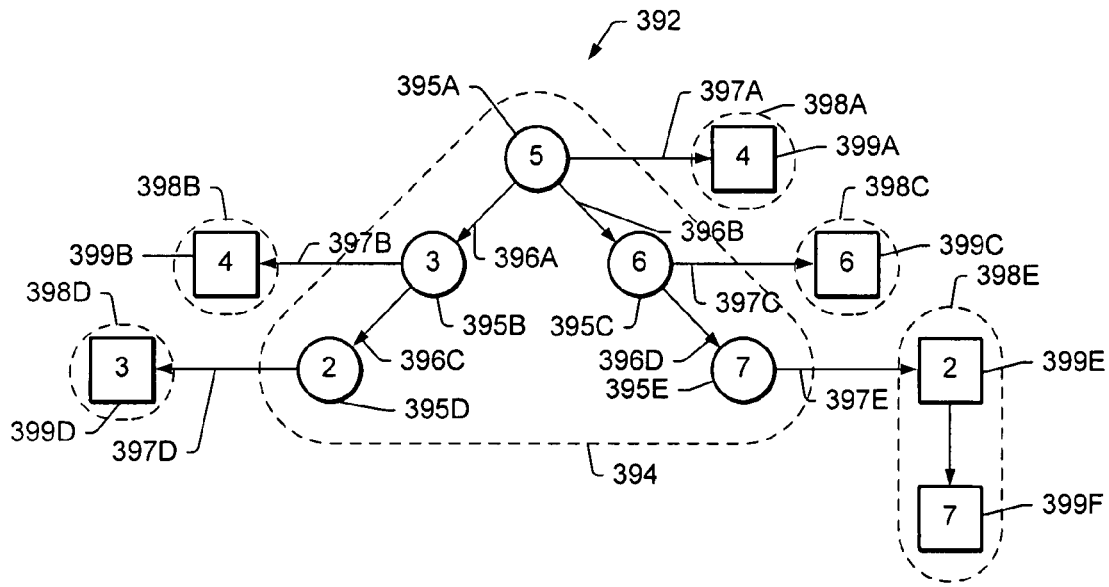
FIG. 3E depicts one embodiment of a sparse data structure implemented using a tree of trees.

Turning now to FIG. 3E, another embodiment of a sparse data structure is shown. Data structure 392 is a self-balancing binary "tree of trees." As with sparse data structures previously described, tree of trees 392 stores, in one embodiment, coordinate pairs representing matches between characters in sequences 102. Tree of trees 392 includes a "base" tree 394, in which nodes 395 store x coordinates (i.e., character position in sequence A) of matches, as well as left/right pointers 396 to other nodes in base tree 394 and a pointer 397 to a y coordinate tree that stores y coordinates of matches (i.e., character position in sequence B). Various y coordinate trees in data structure 392 are indicated by reference numerals 398 in FIG. 3E. Each node 399 in a y coordinate trees 398 includes a y value of a coordinate pair, and may include left and/or right pointers to other y coordinate nodes (in the case in which there is more than one match for a given x coordinate). Because each entry in tree 394 can point to a y coordinate tree 398, data structure 392 represents a tree of trees.

To add a coordinate pair to data structure 392 in one embodiment, the x coordinate may be added to the base tree 394 in a similar manner to the procedure described above for adding nodes to a binary search tree. Then, the y coordinate may be added to the corresponding y coordinate tree 398 in the same or similar fashion.

When a coordinate pair is added to data structure 392, it may be necessary to rebalance base tree 394 and one of the y coordinate trees 398. These rebalancings may be performed independently of one another. For example, if data structure 392 becomes unbalanced because of a single y coordinate tree 398, only that specific tree 398 need be rebalanced in one embodiment. Alternatively, if the x coordinate base tree 394 becomes unbalanced without unbalancing any of y coordinate trees 398, only tree 394 need be rebalanced. Thus, in one embodiment, the x and y trees may be balanced independent of one another. A variety of algorithms may be employed (e.g., AVL balancing, red-black balancing, etc.) to balance data structure 392.

To search for an entry in data structure 392 in one embodiment, the x coordinate of the desired entry is used to locate the appropriate x coordinate node 395 in base tree 394. If such a node 395 exists, the corresponding y coordinate tree 398 is then searched using the y coordinate of the desired entry.

In many instances, data structure 392 offers advantages in memory usage and access time relative to other data structures. As described above, sparse, tree-based data structure 392 may be traversed more efficiently than a dense data structure (and also requires a smaller memory footprint). Furthermore, because data structure 392 is implemented as a binary search tree, it may allow for a faster search time than other sparse data structures. Data structure 392 has a sequentially ordered structure that allows for a search time of O(log N) where N is the number of coordinate pairs in the data structure. In contrast, list 342 has an access time of O(N). Due to the fact that data structure 392 is self-balancing, it also has an average insertion time of O(log N). Other tree-based data structures (e.g., kd-trees), cannot be rebalanced, resulting in longer insertion times. The use of sparse data structure 392 may thus permit a sequence matching algorithm with improved speed and memory efficiency.

Figure 4A:
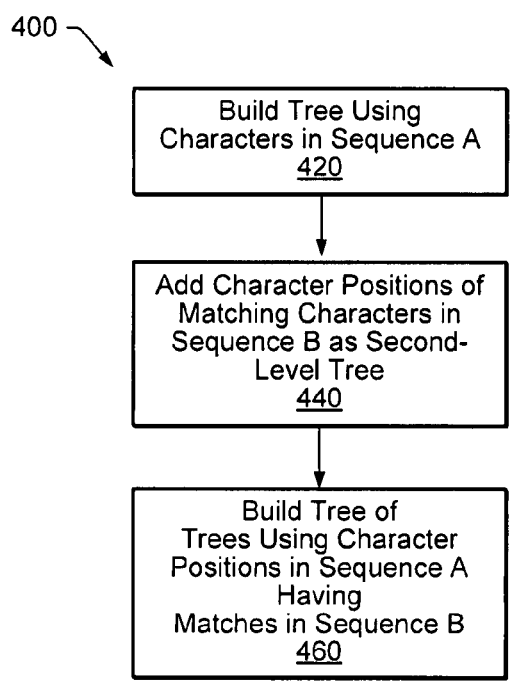
FIG. 4A is a flowchart of one embodiment of a method for building a sparse tree of trees.

Turning now to FIG. 4A, a flowchart of method 400 is shown. Method 400 is one embodiment of an algorithm for implementing step 220 of method 200, in which a sparse data structure is constructed to represent matches between two sequences (e.g., "vintner," (referred to here as 102A) and "grinder" (referred to here as 102B)). In step 420, a tree is constructed using characters in sequence 102A. One example of step 420 is described with reference to FIG. 4B below. In one embodiment, the tree of step 420 is a balanced binary search tree. Next, in step 440, the character positions (also referred to herein as "indices") of matching characters in sequence 102B are added to the tree of step 420 as one or more "second-level" trees. An example of step 440 is described below with reference to FIG. 4C. Finally, in step 460, a "tree of trees" is constructed using the character positions in sequence 102A having matches in sequence 102B. An example of step 460 is described below with reference to FIG. 4D.

Figure 4B:
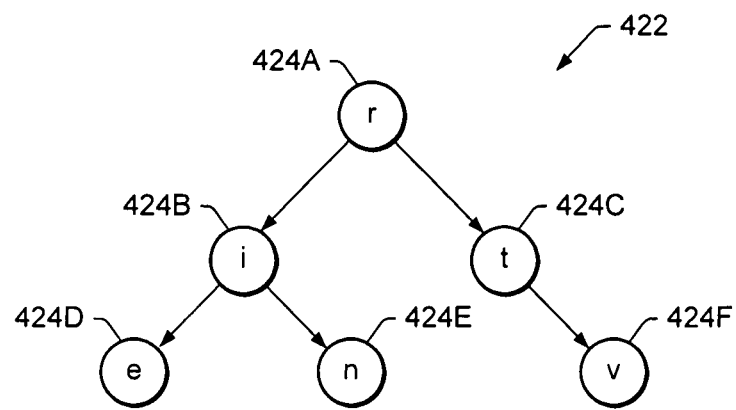
FIGS. 4B-D depicts an example of building a sparse tree of trees.

Turning now to FIG. 4B, one example of a tree 422 that may be constructed in step 420 of method 400 is shown. Consider sequence 102A, "vintner." In this embodiment, tree 422 is a balanced binary search tree with nodes 424A-F that are based on this sequence. (Here, the tree is balanced alphabetically, with the root node storing the letter "r.") Note that the "n" in "vintner," which appears in sequence 102A more than once, appears only once in tree 422 in this embodiment.

Figure 4C:
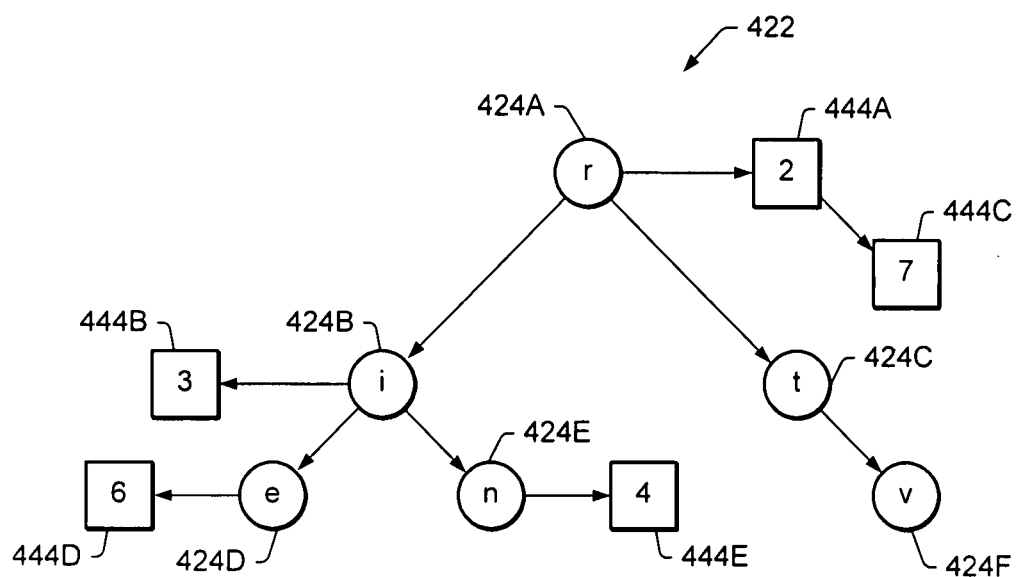

Turning now to FIG. 4C, an example of step 440 of method 400 as applied to tree 422 is shown. In step 440, tree 422 is searched using, in turn, each character in sequence 102B. If a particular character in sequence 102B is not present in the nodes of tree 422 (e.g., the "g" in "grinder"), then tree 422 is not modified. If a particular character in sequence 102B is found in tree 422, however, the index of that character in sequence 102B is added to a second-level tree 444 originating from the node in tree 422 where the character from sequence 102B was found. For example, the letter "i" is in the third character position of sequence 102B. Accordingly, when tree 422 is searched for an "i," and this character is found at node 424B, the index 3 is added to tree 422 as a second-level tree. The index 3 is stored at node 444B. Note that node 424A ("r") has a pointer to index 2 (node 444A), which in turn has a pointer to index 7 (node 444C)—this is because the character "r" appears as both of these positions within sequence 102B. Note further that nodes 424C and 424F do not have pointers to indices since the characters "t" and "v" do not appear in sequence 102B. Accordingly, each node 424 (that is, "top-level" nodes) that points to an index (and thus has an associated second-level tree) contains a character that is present in both sequences 102, i.e., a character that belongs to a match. FIG. 4C thus shows tree 422 converted into a tree of trees.

In step 460, a sparse tree of trees 462 is constructed from tree of trees 422. Tree of trees 462 represents only the matches between sequences 102, and thus can be considered a "match" tree of trees. Because the character positions of each match are stored in match tree of trees 462, it can be considered to store coordinate pairs representing the matches.

Match tree of trees 462 can be constructed in one embodiment as follows: First, tree of trees 422 is searched using each character from sequence 102A (i.e., "v," "i," etc.). Because tree 422 was built using characters from sequence 102A, each character will be found at some node in tree 422. If a character is found at a node that does not have an associated second-level tree (e.g., 424C, which stores the value "t"), that node is not added to tree of trees 462. If, on the other hand, a character from sequence 102A is found at a node in tree 422 that does have an associated second-level tree (e.g., 424B, which stores the value "i"), the index of that character in sequence A (character position 2) is added to a new node of a top-level tree of the tree of trees 462 being constructed. Next, the second-level tree in tree 422 that the just-added node (e.g., 424B) pointed to is copied to tree of trees 462. This process repeats for all characters in sequence 102A. If the addition of each node is self-balancing (e.g., an insertion sort algorithm for an AVL tree), the resulting tree of trees 462 is balanced after all characters from sequence 102A are used to search 422 and insert nodes in tree of trees 462. Unlike tree of trees 422, match tree of trees 462 does not include first-level nodes that do not point to a second-level tree.

Figure 4D:
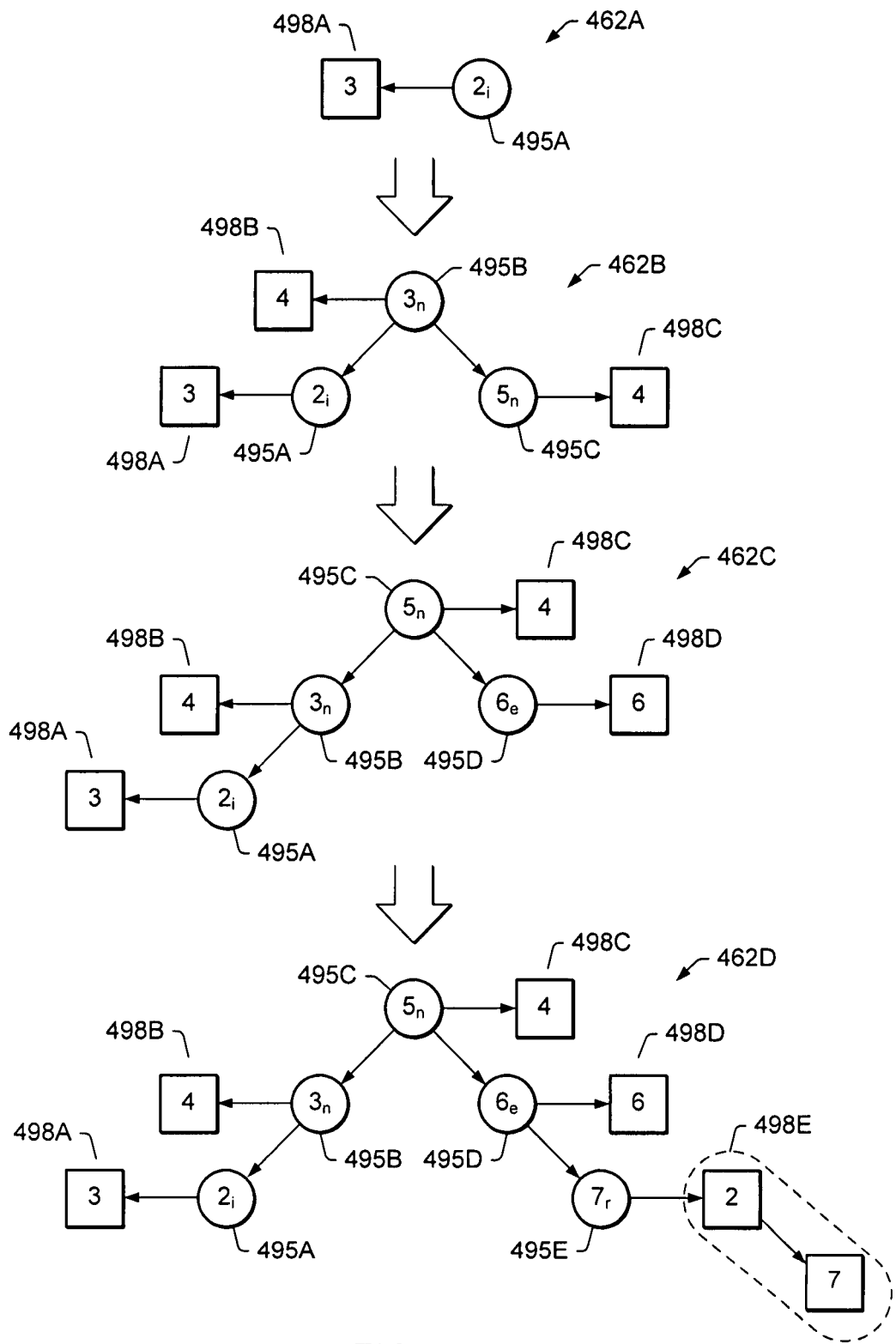

Turning now to FIG. 4D, an example of building a match tree of trees 462 from tree of trees 422 is shown. The first node added to data structure 462 is 495A, which represents the "i" character in sequence 102A found at position 2 (thus shown as $2_i$ in FIG. 4D). Node 495A also points to its associated second-level tree (which references index 3 in sequence 102B) that is copied from tree 422. This second level tree is represented in FIG. 4D by reference numeral 498A. Nodes 495B ($3_n$) and 495C ($5_n$) are added next, followed by nodes 495D ($6_e$) and 495E ($7_r$). Each of the corresponding associated second-level trees from 422 is also copied to data structure 492 as a second-level tree 498. The result is a balanced, sparse data structure indicating 1) the indices of the characters in sequence 102A having matches in sequence 102B and 2) the indices of those matching characters in sequence 102B. As can be seen from FIG. 4D, data structure 492 accurately represents the matches between sequences 102A and 102B. Note that match tree of trees 462 need not store, for example, the value "i" at node 495A—the representation $2_i$ is shown in FIG. 4D for clarity. Other embodiments of method 400 are possible.

As described above, a tree of trees is only one possible type of sparse data structure that may be created in step 220 of method 200. Other types of data structures are also possible.

FIG. 5A shows a flowchart of a method 500 for constructing a sparse data structure using a hash table.

Turning now to FIGS. 5A-C, a flowchart of one embodiment of a method 500 for creating a sparse hash table is shown, as well as an example hash table 542. Method 500 is one embodiment of step 220 of method 200 described above with reference to FIG. 2.

In step 520 of method 500, a hash is created associating characters in sequence A with one of the entries in array 526. This step can be illustrated with reference to FIG. 5B. Hash table 542 includes an array 526 shown to have six entries (any arbitrary number is possible of course). Additionally, the characters in sequence A (e.g., 102A) may be presented to hash table 542 as "keys," or inputs to the table. Step 520 refers to the creation of a "hash," which is a function that takes a given key and produces an index or pointer to one of the entries in array 526. For example, hash function 525 maps key 524A ("v") to entry 1 and key 524C ("n") to entry 3.

Next, in step 540, each character in sequence B (e.g., 102B) is provided as a key 524 to hash table 542. For those characters that hash function 525 indicates are in table 542 (that is, in sequence A), that entry in array 526 is set to point to a location storing the index of the character in sequence B. For example, when the "i" in "grinder" is provided as a key to table 542, hash function 525 will return an index to entry 2 in table 542. Because the "i" in grinder is at character position 3 in sequence B, the pointer in entry 2 in table 542 is set to point to a location that stores the index 3. This is shown in FIG. 5B. This step is repeated for each character in sequence B. Note that entries for characters that appear multiple times in sequence B (e.g., "r") will point to a pair of linked values as shown in FIG. 5B.

Finally, in step 560, another hash function 565 is created to permit hashing into table 542 using character positions in sequence A. This step is illustrated with reference to FIG. 5C.

Figure 6A:
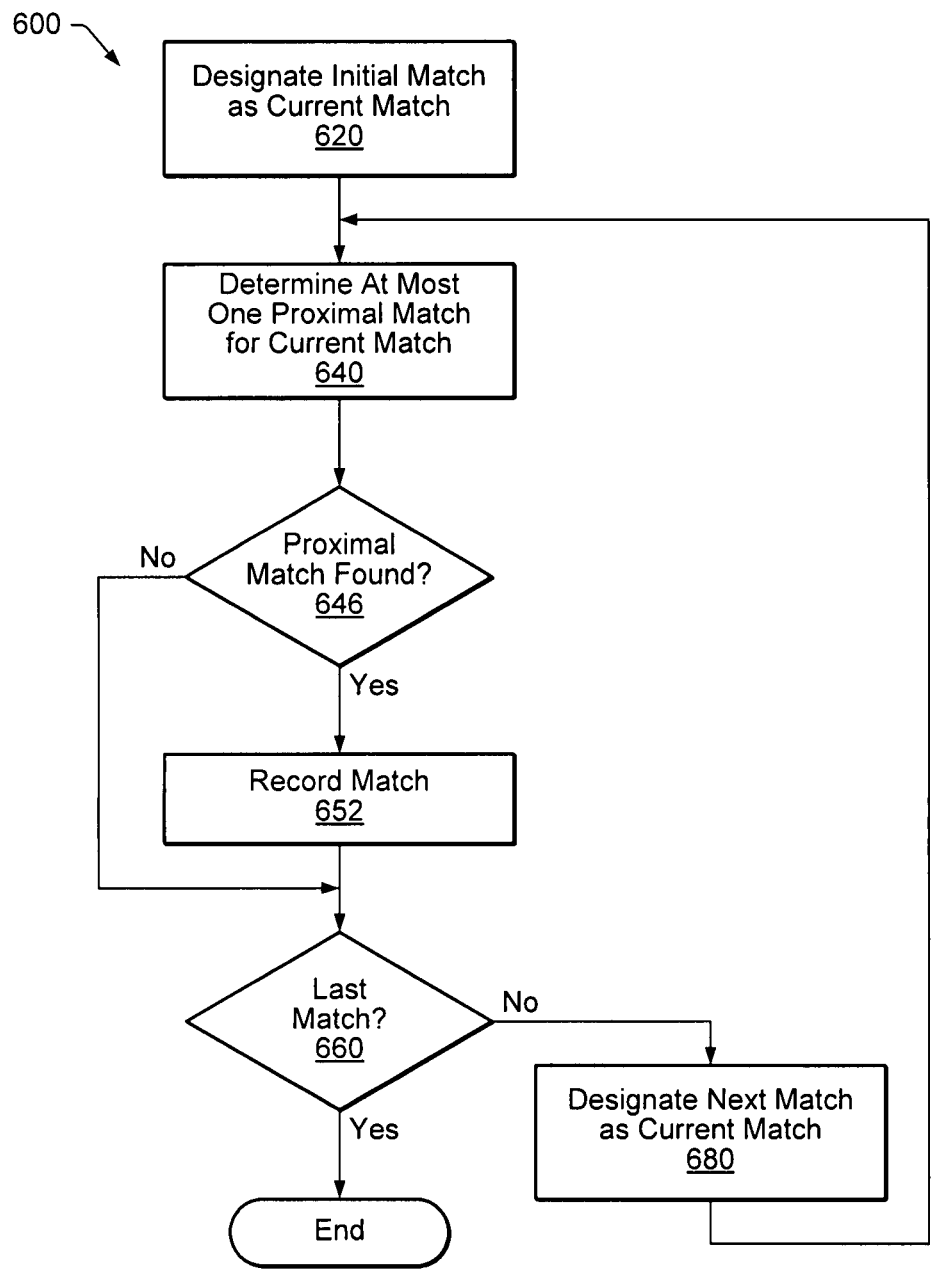
FIG. 6A is a flowchart of one embodiment of a method for linking each match to at most one other match.

Turning now to FIG. 6A, a flowchart for a method 600 is shown. Method 600 is one embodiment of step 240 in method 200, where each match in data structure 222 (where each match in turn is the "current match" in the terminology used below) is linked to at most one other match (referred to as a "local" or "proximal" match), using a local application of some predetermined algorithm. As described below, this predetermined algorithm may be a Smith-Waterman-type scoring algorithm or some algorithm (e.g., a determination of the closest match by distance in an (x,y) coordinate space).

Given a sparse data structure that indicates matches between sequences A and B, an initial match is selected as the "current" match in step 620. This initial match can be any in a set of matches. In one embodiment, this initial match is a match having a coordinate pair with an x value greater than or equal to the x value of all other matches, and with a y value greater than or equal to the y value of all other matches.

Next, in step 640, at most one "proximal" match is determined for the current match. In one embodiment, step 640 includes selecting a region within the (x,y) coordinate space, where the coordinate space includes all the matches. For example, if the current match is at location x,y, the region could be defined as the following coordinates: 1) x+n, y+n (upper left corner of region); 2) x+n+p, y+n (upper right corner); 3) x+n, y+n+p (lower left corner); and 4) x+n+p, y+n+p (lower right corner), where the region is a p×p square in this embodiment. In any event, step 640 includes determining whether any matches are present within the region. Because the region is near the current match in one embodiment, a match (if any) selected from the region is referred to as a "proximal" or "local" match. In one embodiment, the following rules for determining a proximal match apply: 1) if no matches are present, then there is no proximal match for the current match; 2) if there is only one match in the region, that match is the proximal match; and 3) if there is more than one match in the region, then one match is selected as the proximal match according to some predetermined criteria or algorithm. Other rules are possible. Step 640 is described in greater detail with reference to FIGS. 7A-7C below.

Next, in step 646, it is determined whether a proximal match was found. If so, that match is recorded in step 652 (described in greater detail with reference to FIGS. 7E-7G below) and the method proceeds to step 660. Otherwise the method simply proceeds to step 660. In step 660, it is determined whether the current match is the last match to be examined. If so, method 600 ends; otherwise, a next match is designated the current match in step 680 and method 600 returns to step 640.

Figure 6B:
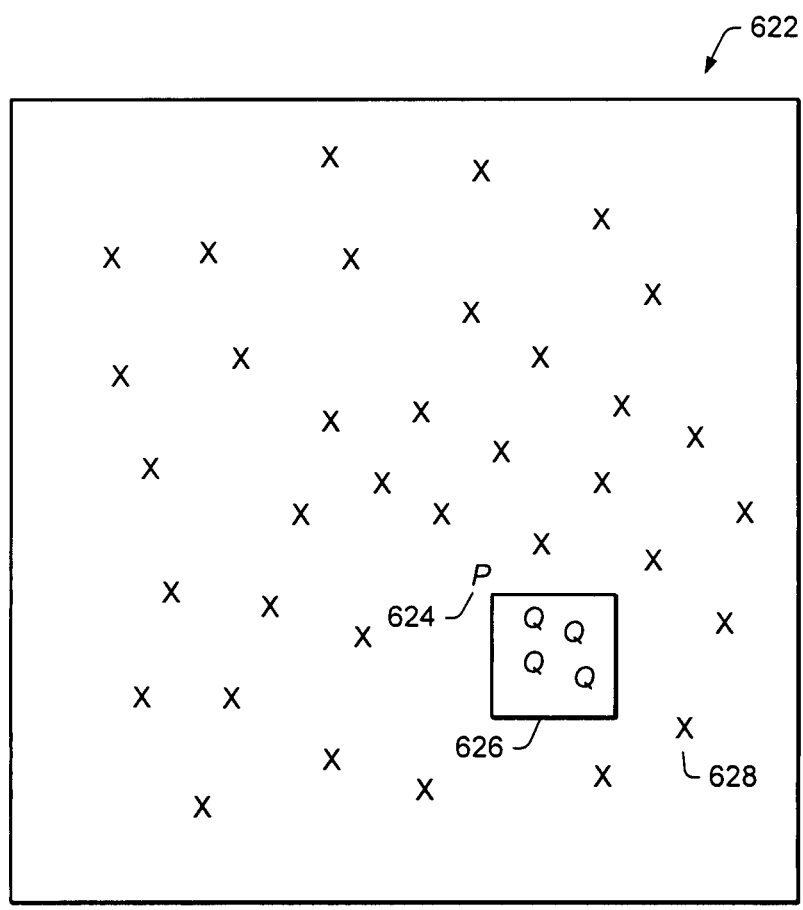
FIG. 6B illustrates the matches Q that are local or proximal to a given match P.

Note that whatever predetermined criteria or algorithm is used, it can be said to be applied "locally" (rather than "globally") because only a portion of the (x,y) coordinate space is examined relative to the current match. This concept can be illustrated with reference to FIG. 6B. FIG. 6B illustrates an (x,y) coordinate space 622 (although x and y axes are not shown). Matches within this space are indicated by X's, P's, and Q's. Match 624 is indicated as P because it is set to be the current match for purposes of the present example. Region 626 of coordinate space 622 is selected relative to current match 624. As shown, there are four matches (Q's) within this region. These four matches are the possible "candidates" for a proximal match to P. One possible algorithm for selecting one of these proximal matches is described below with reference to FIGS. 7A-C. Note that not all matches in coordinate space 622 are guaranteed to have a proximal match, depending on the orientation of the region selected for the current match. For example, if match 628 is the current match and the region for match 628 is selected to have the same orientation as region 626 has to match 624, no proximal match will be found for match 628 in coordinate space 622.

Figure 7A:
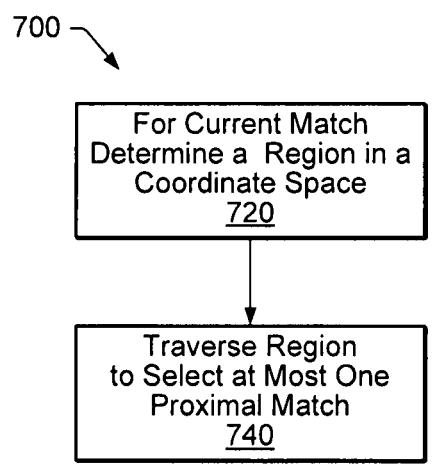
FIG. 7A is a flowchart of one embodiment of a method for determining a proximal match for a current match.

Turning now to FIG. 7A, a flowchart for a method 700 is shown. Method 700 is one embodiment of step 640 in method 600, in which at most one proximal match is determined for the current match. Given a current match, a region in a coordinate plane is determined in step 720. The region can be any arbitrary size and, as described above, is not guaranteed to include any matches. In step 740, the region is traversed in some manner to select at most one match as a proximal match. If more than one proximal match exists, some algorithm is applied to select one of these matches. For example, the region may be traversed in a particular fashion, with the first match encountered being selected as the proximal match. Alternatively, some scoring algorithm (e.g., a Smith-Waterman-type scoring scheme) may be applied to each match in the region, with the match having the highest score selected as the proximal match.

Figure 7B:
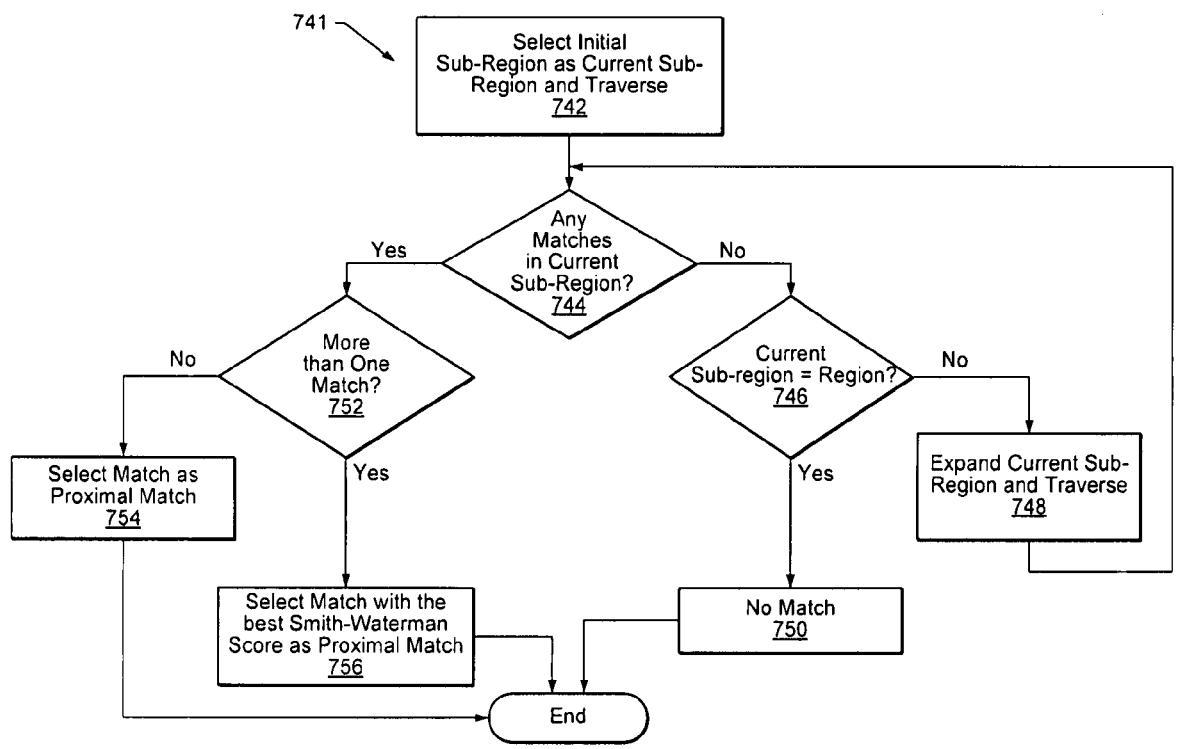
FIG. 7B is a flowchart of one embodiment of a method for traversing a sub-region of an (x,y) coordinate space to select a proximal match.

Turning now to FIG. 7B, a flowchart of one embodiment of a method 741 for traversing the current region is shown. Method 741 begins with step 742, in which an initial "sub-region" of the region is selected as the current sub-region and traversed. If the traversal indicates any matches in step 744, method 741 proceeds to step 752, where it is determined whether more than one match was found. If only one match is found in the current sub-region, that match is selected as the proximal match in step 754. Otherwise, the match with the highest Smith-Waterman score is selected as the proximal match in step 756 in one embodiment (other criteria may of course be used in other embodiments). If no matches are found in step 744, it is determined in step 746 whether the current sub-region is equal to the entire region. If so, method 741 concludes at step 750 with no proximal matches found. Otherwise, the current sub-region is expanded and traversed in step 748, with method 741 then returning to step 744 and continuing as described above until either a sub-region is found with one or matches or the entire region is traversed.

Figure 7C:
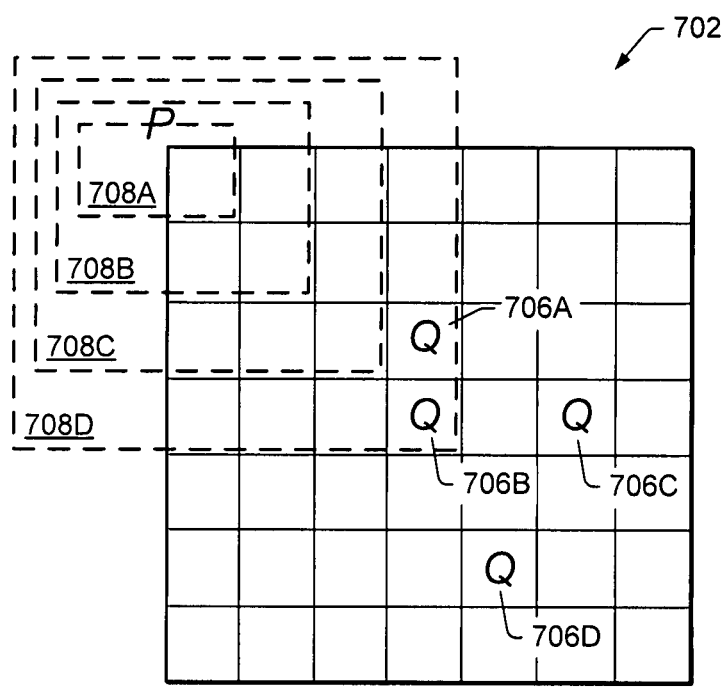
FIG. 7C depicts an example of various sub-regions with a selected region of an (x,y) coordinate space.

Turning now to FIG. 7C, an illustration of one embodiment of method 741 is shown. In this diagram, P represents the current match, Q represents possible proximal matches, and dotted boxes 708 represent a set of expanding square sub-regions. First, an initial 1×1 sub-region (indicated by "1" in FIG. 7C) is selected as the current sub-region and traversed. Because no matches are found in this sub-region, the current sub-region is expanded to a 2×2 sub-region 708B. Again, since no proximal matches exist in sub-region 708B, the current sub-region is expanded (708C) and then expanded again to a 4×4 sub-region 708D. At this point, however, two proximal matches 706A,B exist in the sub-region 708D, so a local application of some algorithm is applied to select one of the matches 706A,B as a proximal match. Other traversals of the region are possible—in various embodiments, it may be desirable to traverse the region in a manner that avoids having to "visit" portions of the region that have already been visited.

Figure 7D:
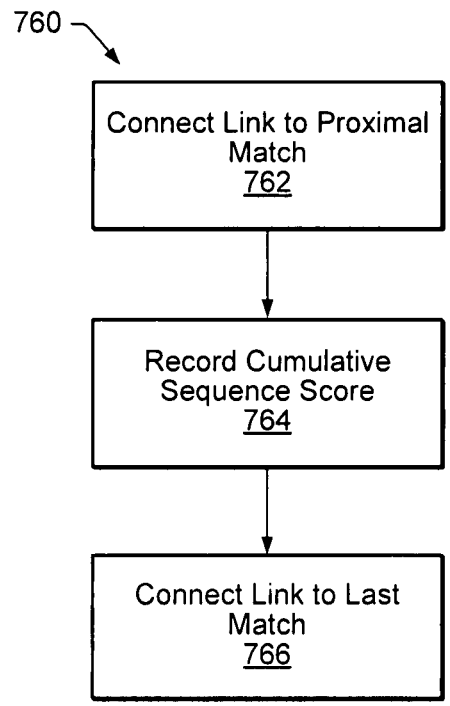
FIG. 7D depicts a flowchart of one embodiment of a method for recording information associated with a proximal match.
Figure 7E:
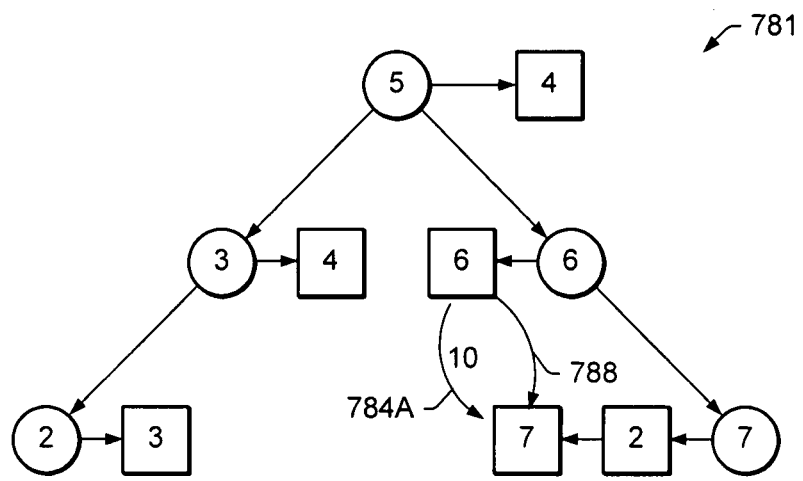
FIG. 7E-F depict an illustration of linking matches within a sparse data structure.
Figure 7F:
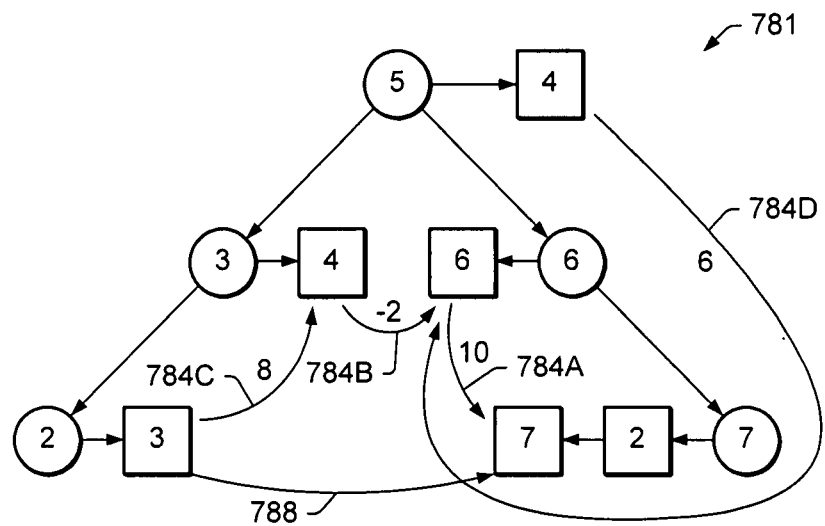

Turning now to FIG. 7D, a flowchart of method 760 is shown. Method 760 is one embodiment of step 652 in method 600 in which a proximal match of a current match is recorded. Method 600 is discussed in conjunction with exemplary tree of trees 781 depicted in FIG. 7E-F. (Method 600 may also be used with other data structures.) In step 762, a link is created in data structure 781 from the current match to its corresponding proximal match. This is depicted in FIG. 7E where reference numeral 784A indicates a link between the match entry at (6,6) to its proximal match at entry (7,7). In step 764, a cumulative sequence score (discussed in greater detail below and depicted as "10" in tree of trees 781) is stored in addition to the link created in step 762. In step 766, a link joining the head entry of the chain to the tail entry is propagated from the proximal match to the current match. In FIG. 7E, link 788 joins the current head of the chain (entry (6,6)) to the tail (entry (7,7)). However, in FIG. 7F, this link 788 is propagated to the new head of the chain (entry (2,3)). The link created in step 766 allows for immediate access to the tail from the head (as opposing to progressing through the entire chain) and may be omitted in other embodiments. FIG. 7F illustrates an exemplary, completed tree of trees 781 generated using one embodiment of method 600. Note that in other embodiments, additional information may be stored in data structure 781 when a proximal match is recorded.

As used herein, the cumulative sequence or link score mentioned above is based on the concept of a "link score" between a given match and its proximal match. The link score is generated using some criteria (Smith-Waterman-type scoring algorithm is used in the example discussed below) based on the number of matches, mismatches and spaces that exist between a current match and a proximal match. For example, the link of current match entry (6,6) and proximal match entry (7,7) contains two matches, no spaces, and no mismatches, so it may receive a link score of 10 (5 points per match). The cumulative score at a given position in a sequence of matches is merely the sum of the individual link scores in the sequence. For example, when entry (3,4) is linked to entry (6,6), the current cumulative link score of 10 is added to the link score between entry (3,4) and entry (6,6) (−12), producing a cumulative link score of −2 (indicated by reference numeral 784B in FIG. 7F.

Figure 7G:
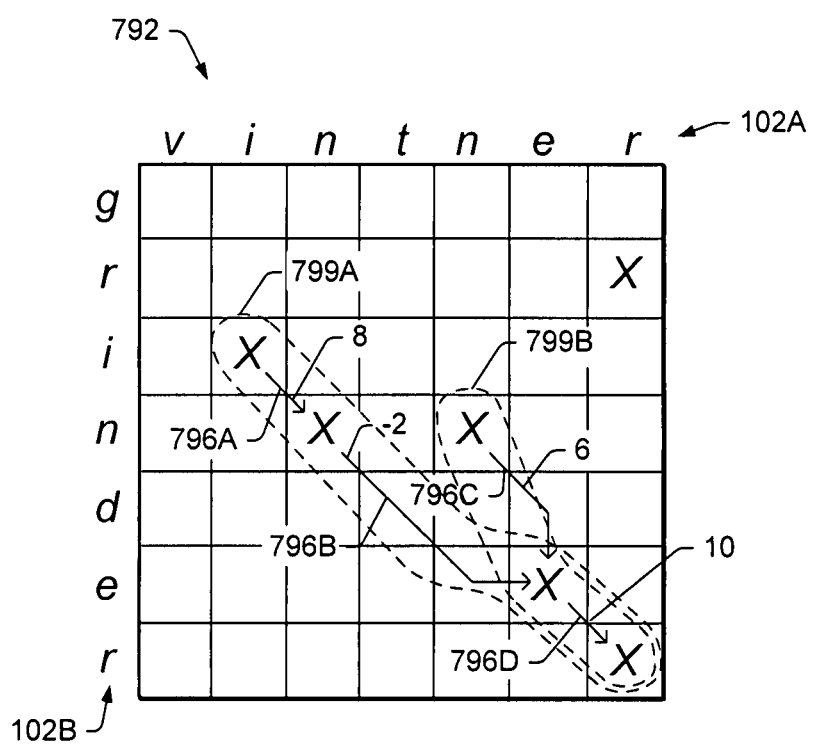
FIG. 7G depicts an example of two chains of matched links for a pair of input sequences.

Turning now to FIG. 7G, two sequences of linked matches are shown for two sample input sequences. As described above, matches between sequences 102 may be represented using a sparse data structure. In this example, the matches between sequences "vintner" and "grinder" are shown relative to an (x,y) coordinate space 792. FIG. 7G shows matches between sequences 102 and the links 796 between proximal matches. Notice that not all matches (e.g. entry (7,1)) have links 796. Note that there are two "chains" of links shown in FIG. 7G: 799A (796A→796B→796D) and 799B (796C→796D). These chains of links represent two possible alignments of sequences 102.

Figures 8A, 8B:
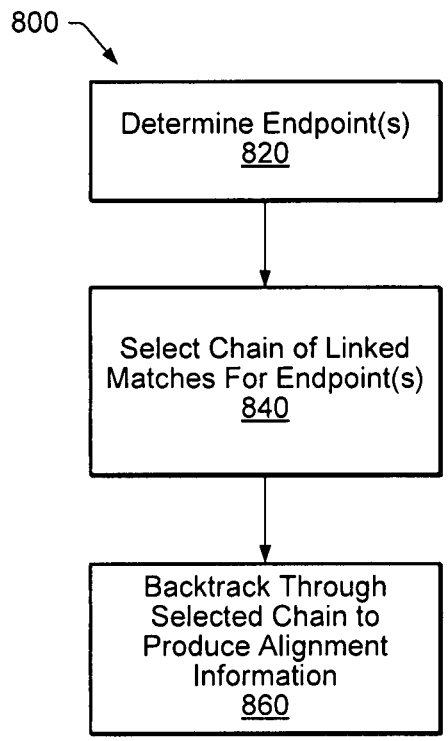
FIG. 8A depicts a flowchart of one embodiment of a method for generating a sequence alignment.
FIG. 8B depicts an alignment generated from an exemplary chain of links.

Turning now to FIG. 8A, a method 800 is shown. Method 800 is one embodiment of step 260 in method 200, where an alignment is determined from the chains or sequences of linked matches created in step 240.

In step 820, a set of end points to be processed is determined. In one embodiment, these endpoints correspond to the last match in each of the chains created in step 240. In another embodiment, the set may contain end points that correspond to chains having high cumulative scores relative to other chains. In other embodiments, other criteria such as the number of matches in a chain, the location of each point, etc. may determine the set of end points. In general, end points may be determined according to a variety of well-known techniques.

In step 840, a chain of linked matches is selected for each endpoint. If only one endpoint is determined in step 820, the chain with the highest cumulative score at that endpoint is selected. For example, in FIG. 7G (described above) two chains 799A and 799B exist that share a common endpoint at entry 7,7. Because chain 799A (score=8) has a higher score than endpoint 799B (score=6), chain 799A is selected.

If more than one endpoint is selected in step 820, an algorithm may be used to filter the chains and make a selection. In one embodiment, this process is performed by generating a key for each of the chains by concatenating the (x,y) coordinate values for each endpoint. The key and cumulative match score for each chain are then added to a tree. If more than one chain has the same key (i.e., share a common endpoint), only the chain having the highest cumulative match score remains in the tree. To filter out the highest cumulative score, the tree of trees is balanced based on cumulative scores, and the cumulative scores are reported from highest to lowest (or lowest to highest). When every chain corresponding to an endpoint is inserted into the tree, the chain with the highest score is selected. It is noted that in other embodiments more than one chain may be selected to determine more than one alignment.

In step 860, once a chain is selected, an algorithm is used to "backtrack" through the chain to produce alignment information (i.e., whether and where gaps are to be inserted into the input sequences). In one embodiment, the backtracking algorithm is a well-known type of Smith-Waterman back tracking algorithm that takes an endpoint and a cumulative sequence score as input and produces corresponding alignment information. For example, FIG. 8B shows the result of the alignment produced from chain 799A shown in FIG. 7G. It is noted that alignment 104A corresponds to the underlined characters in the sequences "vintner" and "grinder" (The "v-" and the "gr" are shown only to display all the characters from "vintner" and "grinder" and are not the result of an alignment generated in an embodiment of step 860).

Figure 8C:
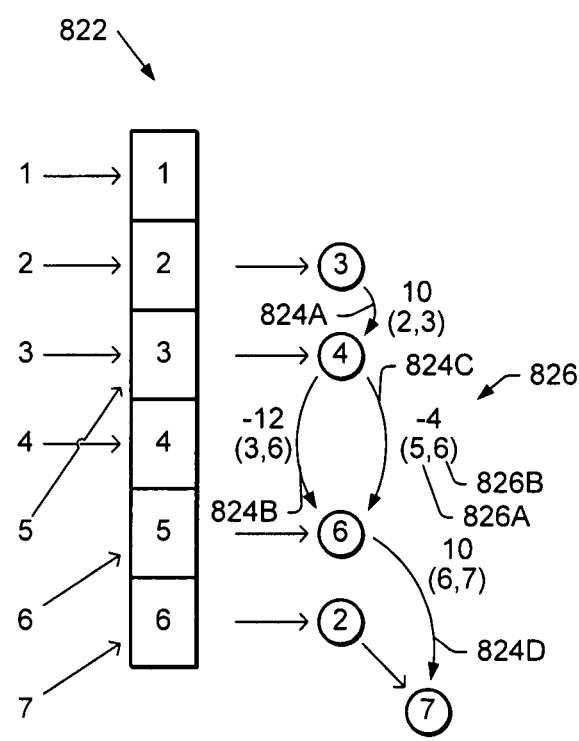
FIG. 8C depicts one embodiment of a hash table with matched links.
Figure 9:
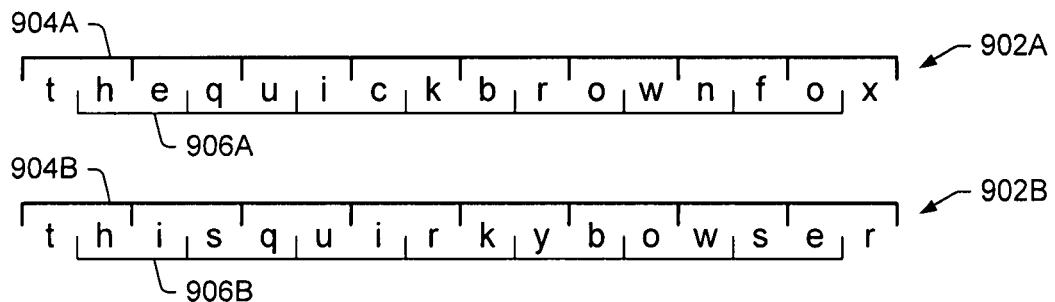
FIG. 9 illustrates the use of multiplet matching.

Turning now to FIG. 8C, another data structure 822 for one embodiment of step 240 is shown. Data structure 822 is a hash table (described above in reference to FIG. 5A-C) that is an alternate embodiment to the tree of trees (depicted in FIG. 7F). In the example, two possible alignments 824A,B,D and 824C,D are shown that are representative of alignments 799A and 799B depicted in FIG. 7G. In a similar manner to tree of trees 781, each link 824 in the alignment represents a link of a match to its proximal match, and a cumulative sequence score is calculated for each alignment. However, in contrast to tree of trees 781, each link 824 in the alignment also contains a source x coordinate 826A and a destination x coordinate 826B. For example, 824A represents a link between entries (2,3) and entries (3,4), so the source x coordinate is 2 and the destination x coordinate is 3. Once each match is linked to at most one proximal match and a corresponding cumulative score is generated, an alignment is determined using method 800.

Embodiments of the sequence-matching algorithm described in this disclosure may offer a significant improvement over a classic Smith-Waterman matching algorithm. For example, when comparing two sequences that are longer than $2^{23}$ characters (one-fourth the length of a human chromosome), embodiments described in the present disclosure may execute 1,000 to 10,000 times faster than the Smith-Waterman algorithm (and use considerably less memory).

When sequences A and B comprising M and N characters chosen from an alphabet of S characters where matches are considered for P characters at a time, the Smith-Waterman algorithm has O(MN) overall computational complexity. The use of a sparse data structure and the linking of a match to at most one other match using a local application of an algorithm (as opposing to the linking of a match to all other matches using a global application of an algorithm) in the various embodiments described above, however, may result in an algorithm with complexity $O[(M+N) \log(M) + MN/S^P + MN/S^P \log(MN/S^P)]$ where $(M+N) \log (M)$ is the computational complexity for building and searching a first level tree (depicted in FIG. 4B), $MN/S^P$ is the computational complexity for copying second level trees into the first tree (i.e., convert a tree to a tree of trees (depicted in FIG. 4C)), and $MN/S^P \log(MN/S^P)$ is the computational complexity for building and searching a new tree of trees (depicted in 7F). This computational complexity in affect reduces to an overall computational complexity of $O[(M+N)\log(M)]$ Although some of the examples provided above focus on matches between single characters in sequences 102 ("singlet" matching), method 200 and the term "match" are not limited to matching one character at a time. The disclosed sequence matching techniques may be applied, for instance, to attempt to match multiple characters at a time between two sequences ("multiplet" matching). Consider FIG. 9, in which sequence 902A ("thequickbrownfox") and sequence 902B ("thisquirkybowser") are divided into character pairs by "reading frames" 904 and 906. In this embodiment, all characters in a pair must be equivalent to those in another in order to be constituted as a match. For example, the "th" in 904A matches the "th" in 904B.

Sequence matching using multiplet matching is similar to singlet matching, but does include some differences. For example, in building the sparse data structure of step 220, the data structure is built using character pairs in sequence 902A from both reading frames 904 and 906. For example, a sparse data structure may include character pairs "th," "he," "eq," etc. Furthermore, when adding matching character positions from sequence 902B to the sparse data structure, the data structure is searched using characters from both reading frames of sequence 902B. For example, in the context of FIG. 9, the character pairs "th," "hi," "is," etc. are used to search the previously created sparse data structure in order to add the positions of matching character pairs. From that point, sequence matching is performed similar to embodiments described above. It is noted that matches of character sequences that are smaller than the divisions created by the reading frames may not be detected and included in the sparse data structure unless a smaller localized application of a sequence matching algorithm is applied (e.g. the letter "k" in sequences 902 will not be detected in a reading frame with divisions containing 2 characters).

Multiplet matching may also be used, for example, to reduce the probability of so-called random matches. For example, in certain contexts (e.g., genetic sequence matching), it may not be desirable to designate a match between two sequences unless the match is at least X characters long, where X is an integer greater than or equal to two. By using multiplet matching, an "isolated" match of a single character will not be recorded.

Figure 10:
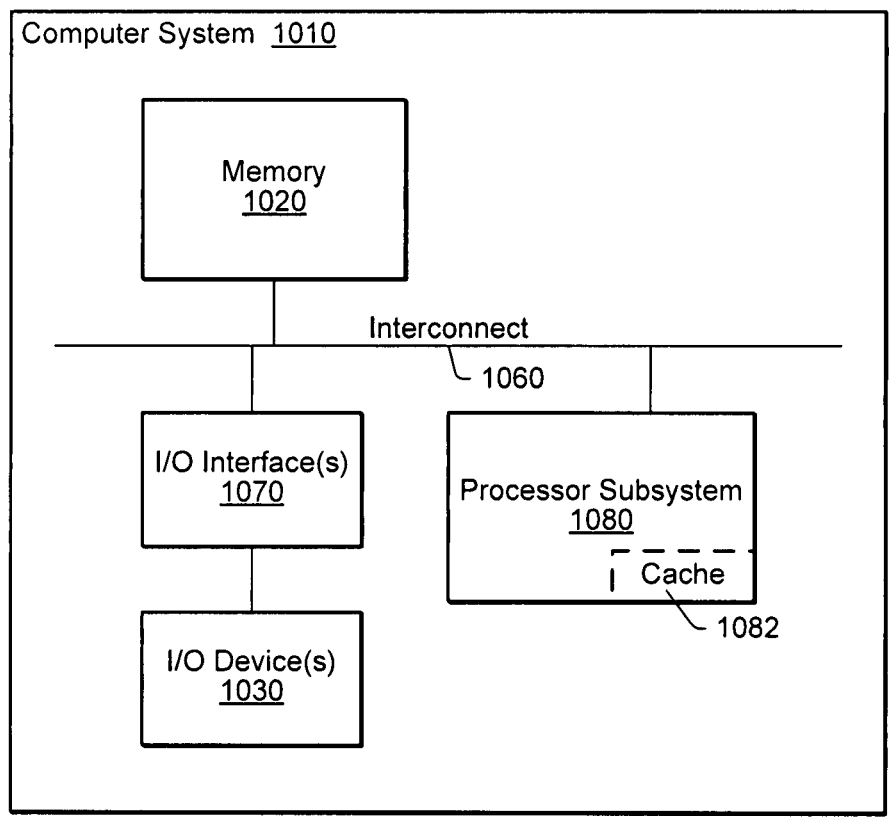
FIG. 10 is block diagram of one embodiment of a computer system or computing device for performing a sequence-matching algorithm.

The sequence-matching embodiments described above may be performed on any suitable type of computer system, which includes any type of computing device. FIG. 10 illustrates one embodiment of a computer system 1010 that may be used to implement the above-described techniques. As shown, computer system 1010 includes a processor subsystem 1080 (which may have a cache 1082 in one embodiment) that is coupled to a memory 1020 and I/O interfaces(s) 1070 via an interconnect 1060 (e.g., a system bus). I/O interface(s) 1070 is coupled to one or more I/O devices 1030. Computer system 1010 may be any of various types of devices, including, but not limited to, a personal computer system, desktop computer, laptop or notebook computer, mainframe computer system, handheld computer, workstation, network computer, a consumer device such as a mobile phone, pager, or personal data assistant (PDA). Computer system 1010 may also be any type of networked peripheral device such as storage devices, switches, modems, routers, etc. Although a single computer system 1010 is shown in FIG. 10, system 1010 may also be implemented as two or more computer systems operating together.

Processor subsystem 1080 may include one or more processors or processing units. For example, processor subsystem 1080 may include one or more multi-processor cores, each with its own internal communication and buses. In various embodiments of computer system 1010, multiple instances of processor subsystem 1080 may be coupled to interconnect 1060. In various embodiments, processor subsystem 1080 (or each processing unit within 1080) may contain a cache 1082 or other form of on-board memory.

Computer system 1010 also contains memory 1020 which is usable by processor subsystem 1080. Memory 1020 may be implemented using different physical memory media, such as hard disk storage, floppy disk storage, removable disk storage, flash memory, random access memory (RAM-SRAM, EDO RAM, SDRAM, DDR SDRAM, Rambus® RAM, etc.), ROM (PROM, EEPROM, etc.), and so on.

I/O interfaces 1070 may be any of various types of interfaces configured to couple to and communicate with other devices, according to various embodiments. In one embodiment, I/O interface 1070 is a bridge chip from a front-side to one or more back-side buses.

I/O interfaces 1070 may be coupled to one or more I/O devices 1030 via one or more corresponding buses or other interfaces. Examples of I/O devices include storage devices (hard drive, optical drive, removable flash drive, storage array, SAN, or their associated controller), network interface devices (e.g., to a local or wide-area network), or other devices (e.g., graphics, user interface devices, etc.)

Memory in computer system 1010 is not limited to memory 1020. Rather, computer system 1010 may be said to have a "memory subsystem" that includes various types/locations of memory. For example, the memory subsystem of computer system 1010 may, in one embodiment, include memory 1020, cache 1082 in processor subsystem 1080, and storage on I/O Devices 1030 (e.g., a hard drive, storage array, etc.). Thus, the phrase "memory subsystem" is representative of various types of possible memory media within computer system 1010. In some embodiments, the memory subsystem includes program instructions executable by processor subsystem 1080 to perform embodiments of the sequence matching algorithms of the present disclosure.

Various embodiments of the sequence-matching algorithm (described above) may include storing instructions and/or data implemented in accordance with the foregoing description in an article of manufacture such as a tangible computer-readable memory medium, including various portions of the memory subsystem of computer system 1010. Certain embodiments of these tangible computer-readable memory media may store instructions and/or data that are computer executable to perform actions in accordance with the present disclosure. Generally speaking, such an article of manufacture may include storage media or memory media such as magnetic (e.g., disk) or optical media (e.g., CD, DVD, and related technologies, etc.). The article of manufacture may be either volatile or nonvolatile memory. For example, the article of manufacture may be (without limitation) SDRAM, DDR SDRAM, RDRAM, SRAM, flash memory, and of various types of ROM, etc.

Further embodiments may include signals such as electrical, electromagnetic, or optical signals, conveyed via a communication medium, link, and/or system (e.g., cable, network, etc.), whether wired, wireless or both. Such signals may carry instructions and/or data implemented in accordance with the foregoing description.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed by various described embodiments. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

What is claimed is:

1. A non-transitory computer-readable medium storing program instructions for determining a first alignment between a first sequence and a second sequence, wherein the program instructions are executable on a computer system to:
   store representations of identified matches between the first and second sequences in a first data structure on the computer system, wherein the first data structure is a sparse data structure;
   store information linking each identified match in the first data structure to at most one other match in the first data structure based on a local application of a first algorithm; and determine the first alignment using stored information indicative of one or more sequences of linked matches; and store an indication of the first alignment on the computer system.

2. The non-transitory computer-readable medium of claim 1, wherein the program instructions are executable by the computer system to construct the first data structure, wherein the first data structure is a tree of trees, and wherein the program instructions are executable to store a representation of a given identified match between a set of characters in the first and second sequences by storing the respective positions of the set of characters in both the first and second sequences.

3. The non-transitory computer-readable medium of claim 2, wherein the tree of trees is self-balancing.

4. The non-transitory computer-readable medium of claim 1, wherein the program instructions are executable to identify a first match between a set of one or more characters in the first and second sequences according to a matching algorithm.

5. The non-transitory computer-readable medium of claim 4, wherein the matching algorithm uses synonyms.

6. The non-transitory computer-readable medium of claim 1, wherein the first data structure is a hash table.

7. The non-transitory computer-readable medium of claim 1, wherein the first algorithm uses a Smith-Waterman-type scoring scheme.

8. The non-transitory computer-readable medium of claim 7, wherein the stored representations for a given identified match are coordinate pairs corresponding to the respective character positions of the given identified match in each of the first and second sequences, and wherein the first algorithm includes computing the distance between a pair of matches using the corresponding coordinate pairs for each match.

9. A non-transitory computer-readable medium storing program instructions executable by a computer system to:
   access a first data structure storing information representing matches in first and second input sequences, wherein the first data structure stores, for each match, a coordinate pair identifying a point in an (x, y) coordinate space, wherein the coordinate pair is indicative of the respective positions of the match in each of the first and second input sequences;
   for each match represented in the first data structure, determine whether any proximal matches exist within the first data structure, and, if so, store information to the first data structure linking that match to a single one of the determined proximal matches;
   wherein the information stored in the first data structure indicative of linked matches is usable to perform an alignment operation on the first and second input sequences.

10. The non-transitory computer-readable medium of claim 9, wherein the program instructions executable to determine whether any proximal matches exist for a given match include instructions executable to:
   select a first region within the (x, y) coordinate space, wherein the first region is local relative to an (x, y) coordinate pair corresponding to the given match in the first data structure;
   traverse the first region to determine at most one proximal match for the given match.

11. The non-transitory computer-readable medium of claim 10, wherein the first region is a square.

12. The non-transitory computer-readable medium of claim 11, wherein the program instructions executable to traverse the first region to determine whether any proximal matches exist for a given match include program instructions executable to:
   beginning with a first sub-region within the first region, select successively larger sub-regions of the first region until a sub-region is found with at least one proximal match; and
   if a current sub-region has at least one proximal match:
      if the sub-region includes a single proximal match, link the single proximal match to the given match in the first data structure;
      if the sub-region includes a plurality of proximal matches, select one of the plurality of proximal matches using a first algorithm and link the selected proximal match to the given match in the first data structure.

13. The non-transitory computer-readable medium of claim 12, wherein the first algorithm includes:
   computing a score for each of the plurality of proximal matches in the current sub-region, wherein the score is computed according to a Smith-Waterman-type scoring scheme;
   selecting the one of the plurality of proximal matches having the highest computed score.

14. A non-transitory computer-readable medium storing program instructions executable by a computer system to:
   receive first and second input sequences to be aligned;
   populate entries in a sparse data structure with (x, y) coordinate information for corresponding matches between character sets in the first and second input sequences, wherein, for a given entry, the x coordinate corresponds to a position of a character set in the first input sequence and the y coordinate corresponds to a position of the character set in the second input sequence; and
   use the (x, y) coordinate information within the sparse data structure to perform an alignment operation on the first and second input sequences, wherein the use of the (x, y) coordinate information includes:
      linking each match represented in the sparse data structure to at most one other match, wherein a given match is linked to the at most one other match based at least in cart upon an (x, y) distance between the given match and the at most one other match.

15. The non-transitory computer-readable medium of claim 14, wherein the sparse data structure is a self-balancing, tree-based data structure.

16. The non-transitory computer-readable medium of claim 14, wherein the use of the (x, y) coordinate information within the sparse data structure to perform an alignment operation further includes:
   selecting one or more sequences of linked matches, wherein the selected one or more sequences are usable to determine gaps to be inserted into either or both of the first and second input sequences as part of the alignment operation.

17. The non-transitory computer-readable medium of claim 14, wherein the program instructions executable to populate entries in the sparse data structure include program instructions executable to:
   build a first tree-based data structure with entries including characters in the first input sequence;
   for each entry in the first data structure corresponding to character sets in the first input sequence with one or more matches in the second input sequence, add one or more values indicative of the corresponding character positions of the one or more matches in the second input sequence; and build the sparse data structure using character positions in the first input sequence having matches in the second input sequence.

18. The non-transitory computer-readable medium of claim 14, wherein the program instructions are executable to perform multiple matches.

* * * * *

UNITED STATES PATENT AND TRADEMARK OFFICE
CERTIFICATE OF CORRECTION

PATENT NO. : 8,965,935 B2
APPLICATION NO. : 11/937315
DATED : February 24, 2015
INVENTOR(S) : Brown It is certified that error appears in the above-identified patent and that said Letters Patent is hereby corrected as shown below:

IN THE SPECIFICATION

In column 5, line 22, delete "($S_{x,y}$) The" and insert -- ($S_{x,y}$). The --, therefor.

In column 16, line 37, delete "O[(M+N)log(M)]" and insert -- O[(M+N)log(M)]. --, therefor.

IN THE CLAIMS

In column 20, line 42, in Claim 14, delete "cart" and insert -- part --, therefor.

In column 20, line 57, in Claim 17, delete "claim 14," and insert -- claim 15, --, therefor.

In column 21, line 6, in Claim 18, delete "multiple" and insert -- multiplet --, therefor.

Signed and Sealed this
Twentieth Day of October, 2015

Michelle K. Lee
*Director of the United States Patent and Trademark Office*